US008801783B2

(12) United States Patent
Stone et al.

(10) Patent No.: US 8,801,783 B2
(45) Date of Patent: *Aug. 12, 2014

(54) PROSTHETIC LIGAMENT SYSTEM FOR KNEE JOINT

(75) Inventors: Kevin T. Stone, Winona Lake, IN (US); Robert Metzger, Wakarusa, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 545 days.

This patent is subject to a terminal disclaimer.

(21) Appl. No.: 12/788,978

(22) Filed: May 27, 2010

(65) Prior Publication Data

US 2010/0292792 A1 Nov. 18, 2010

Related U.S. Application Data

(63) Continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,405, filed on Aug. 22, 2008, (Continued)

(51) Int. Cl.
*A61F 2/08* (2006.01)

(52) U.S. Cl.
USPC .................................. 623/13.14; 623/13.13

(58) Field of Classification Search
CPC ............ A61F 2/08; A61B 17/04; A61L 17/00
USPC ............... 623/13.11–13.2; 606/151, 228–232
See application file for complete search history.

(56) References Cited

U.S. PATENT DOCUMENTS

| 26,501 A | 12/1859 | Kendrick et al. |
| 65,499 A | 6/1867 | Miller |

(Continued)

FOREIGN PATENT DOCUMENTS

| AU | 4957264 | 3/1966 |
| AU | 440266 | 10/1967 |

(Continued)

OTHER PUBLICATIONS

"AperFix® System Surgical Technique Guide. Single Tunnel Double Bundle.™" Cayenne Medical brochure. (Aug. 2008) 8 sheets.

(Continued)

*Primary Examiner* — Andrew Iwamaye
(74) *Attorney, Agent, or Firm* — Harness, Dickey

(57) ABSTRACT

A system for a knee joint includes a first fastener and a second fastener operable to be connected to the tibia and femur, respectively. Furthermore, the system includes a flexible prosthetic ligament member. The ligament member is operably coupled to the first and second fasteners to support the tibia and the femur for relative movement. The ligament member extends from a first end to a second end, and includes an outer wall that defines a hollow longitudinal passage portion. The first end extends into and out of the longitudinal passage portion through the outer wall to define a first adjustable loop, and the second end extends into and out of the longitudinal passage portion through the outer wall to define a second adjustable loop.

17 Claims, 11 Drawing Sheets

Related U.S. Application Data now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 11/541,506, filed on Sep. 29, 2006, now Pat. No. 7,601,165, application No. 12/788,978, which is a continuation-in-part of application No. 12/570,854, filed on Sep. 30, 2009, now Pat. No. 8,303,604, which is a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, application No. 12/788,978, which is a continuation-in-part of application No. 12/702,067, filed on Feb. 8, 2010, now Pat. No. 8,672,968, which is a continuation of application No. 11/541,505, filed on Sep. 29, 2006, now Pat. No. 7,658,751, application No. 12/788,978, which is a continuation-in-part of application No. 12/196,398, filed on Aug. 22, 2008, now Pat. No. 7,959,650, which is a continuation-in-part of application No. 11/784,821, filed on Apr. 10, 2007.

(56) References Cited

U.S. PATENT DOCUMENTS

| | | |
|---|---|---|
| 126,366 A | 4/1872 | Wills |
| 233,475 A | 10/1880 | Cook et al. |
| 261,501 A | 7/1882 | Vandermark |
| 268,407 A | 12/1882 | Hughes |
| 330,087 A | 11/1885 | Binns |
| 417,805 A | 12/1889 | Beaman |
| 487,304 A | 12/1892 | Todd |
| 762,710 A | 6/1904 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 401,677 A | 11/1933 | Roeder |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Drit |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majztin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex et al. |

(56) References Cited

U.S. PATENT DOCUMENTS

| | | |
|---|---|---|
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,146,022 A | 3/1979 | Johnson et al. |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson et al. |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |

(56) References Cited

U.S. PATENT DOCUMENTS

| | | | |
|---|---|---|---|
| 4,870,957 | A | 10/1989 | Goble et al. |
| 4,873,976 | A | 10/1989 | Schreiber |
| 4,887,601 | A | 12/1989 | Richards |
| 4,889,110 | A | 12/1989 | Galline et al. |
| 4,890,615 | A | 1/1990 | Caspari et al. |
| 4,893,619 | A | 1/1990 | Dale et al. |
| 4,893,974 | A | 1/1990 | Fischer et al. |
| 4,895,148 | A | 1/1990 | Bays et al. |
| 4,896,668 | A | 1/1990 | Popoff et al. |
| 4,898,156 | A | 2/1990 | Gatturna et al. |
| 4,899,743 | A | 2/1990 | Nicholson et al. |
| 4,901,721 | A | 2/1990 | Hakki |
| 4,922,897 | A | 5/1990 | Sapega et al. |
| 4,923,461 | A | 5/1990 | Caspari et al. |
| 4,927,421 | A | 5/1990 | Goble et al. |
| 4,946,377 | A | 8/1990 | Kovach |
| 4,946,468 | A | 8/1990 | Li |
| 4,950,270 | A | 8/1990 | Bowman et al. |
| 4,950,285 | A | 8/1990 | Wilk |
| 4,960,381 | A | 10/1990 | Niznick |
| 4,961,741 | A | 10/1990 | Hayhurst |
| 4,968,315 | A | 11/1990 | Gatturna |
| 4,968,317 | A | 11/1990 | Tormala et al. |
| 4,969,886 | A | 11/1990 | Cziffer et al. |
| 4,974,488 | A | 12/1990 | Spralja |
| 4,976,736 | A | 12/1990 | White et al. |
| 4,978,350 | A | 12/1990 | Wagenknecht et al. |
| 4,979,956 | A | 12/1990 | Silvestrini |
| 4,983,176 | A | 1/1991 | Cushman et al. |
| 4,988,351 | A | 1/1991 | Paulos et al. |
| 4,994,074 | A | 2/1991 | Bezwada et al. |
| 4,997,433 | A | 3/1991 | Goble et al. |
| 5,002,550 | A | 3/1991 | Li |
| 5,002,562 | A | 3/1991 | Oberlander |
| 5,002,574 | A | 3/1991 | May et al. |
| 5,007,921 | A | 4/1991 | Brown |
| 5,030,224 | A | 7/1991 | Wright et al. |
| 5,030,235 | A | 7/1991 | Campbell, Jr. |
| 5,035,701 | A | 7/1991 | Kabbara |
| 5,037,422 | A | 8/1991 | Hayhurst et al. |
| 5,037,426 | A | 8/1991 | Goble et al. |
| 5,041,129 | A | 8/1991 | Hayhurst et al. |
| 5,046,513 | A | 9/1991 | Gatturna et al. |
| 5,047,030 | A | 9/1991 | Draenert |
| 5,053,046 | A | 10/1991 | Janese |
| 5,053,047 | A | 10/1991 | Yoon |
| 5,059,201 | A | 10/1991 | Asnis |
| 5,059,206 | A | 10/1991 | Winters |
| 5,061,277 | A | 10/1991 | Carpentier et al. |
| 5,062,344 | A | 11/1991 | Gerker |
| 5,062,843 | A | 11/1991 | Mahony, III |
| 5,064,431 | A | 11/1991 | Gilbertson et al. |
| 5,071,420 | A | 12/1991 | Paulos et al. |
| 5,074,874 | A | 12/1991 | Yoon et al. |
| 5,078,731 | A | 1/1992 | Hayhurst |
| 5,078,843 | A | 1/1992 | Pratt |
| 5,084,050 | A | 1/1992 | Draenert |
| 5,084,058 | A | 1/1992 | Li |
| 5,085,661 | A | 2/1992 | Moss |
| 5,087,263 | A | 2/1992 | Li |
| 5,087,309 | A | 2/1992 | Melton, Jr. |
| 5,089,012 | A | 2/1992 | Prou |
| 5,092,866 | A | 3/1992 | Breard et al. |
| 5,098,435 | A | 3/1992 | Stednitz et al. |
| 5,100,415 | A | 3/1992 | Hayhurst |
| 5,100,417 | A | 3/1992 | Cerier et al. |
| 5,108,433 | A | 4/1992 | May et al. |
| 5,116,337 | A | 5/1992 | Johnson |
| 5,116,373 | A | 5/1992 | Jakob et al. |
| 5,116,375 | A | 5/1992 | Hofmann |
| 5,123,913 | A | 6/1992 | Wilk et al. |
| 5,123,914 | A | 6/1992 | Cope |
| 5,127,785 | A | 7/1992 | Faucher et al. |
| 5,129,901 | A | 7/1992 | Decoste |
| 5,129,902 | A | 7/1992 | Goble et al. |
| 5,129,904 | A | 7/1992 | Illi et al. |
| 5,129,906 | A | 7/1992 | Ross et al. |
| 5,139,498 | A | 8/1992 | Astudillo Ley |
| 5,139,499 | A | 8/1992 | Small et al. |
| 5,139,520 | A | 8/1992 | Rosenberg |
| 5,143,498 | A | 9/1992 | Whitman |
| 5,147,362 | A | 9/1992 | Goble |
| 5,149,329 | A | 9/1992 | Richardson |
| 5,151,104 | A * | 9/1992 | Kenna .......................... 606/328 |
| 5,152,790 | A | 10/1992 | Rosenberg et al. |
| 5,154,189 | A | 10/1992 | Oberlander |
| 5,156,616 | A | 10/1992 | Meadows et al. |
| 5,163,960 | A | 11/1992 | Bonutti |
| D331,626 | S | 12/1992 | Hayhurst et al. |
| 5,169,400 | A | 12/1992 | Muhling et al. |
| 5,176,682 | A | 1/1993 | Chow |
| 5,178,629 | A | 1/1993 | Kammerer |
| 5,183,458 | A | 2/1993 | Marx |
| 5,190,545 | A | 3/1993 | Corsi et al. |
| 5,192,282 | A | 3/1993 | Draenert et al. |
| 5,197,987 | A | 3/1993 | Koch et al. |
| 5,203,784 | A | 4/1993 | Ross et al. |
| 5,203,787 | A | 4/1993 | Noblitt et al. |
| 5,207,679 | A | 5/1993 | Li |
| 5,209,753 | A | 5/1993 | Biedermann et al. |
| 5,209,805 | A | 5/1993 | Spraggins |
| 5,211,647 | A | 5/1993 | Schmieding |
| 5,211,650 | A | 5/1993 | Noda |
| 5,214,987 | A | 6/1993 | Fenton, Sr. |
| 5,219,359 | A | 6/1993 | McQuilkin et al. |
| 5,222,976 | A | 6/1993 | Yoon |
| 5,224,946 | A | 7/1993 | Hayhurst et al. |
| 5,230,699 | A | 7/1993 | Grasinger |
| 5,232,436 | A | 8/1993 | Janevski |
| 5,234,435 | A | 8/1993 | Seagrave, Jr. |
| 5,235,238 | A | 8/1993 | Nomura et al. |
| 5,236,445 | A | 8/1993 | Hayhurst et al. |
| 5,236,461 | A | 8/1993 | Forte |
| 5,242,447 | A | 9/1993 | Borzone |
| 5,246,441 | A | 9/1993 | Ross et al. |
| 5,249,899 | A | 10/1993 | Wilson |
| 5,250,053 | A | 10/1993 | Snyder |
| 5,258,015 | A | 11/1993 | Li et al. |
| 5,258,016 | A | 11/1993 | DiPoto et al. |
| 5,258,040 | A | 11/1993 | Bruchman et al. |
| 5,261,908 | A | 11/1993 | Campbell, Jr. |
| 5,268,001 | A | 12/1993 | Nicholson et al. |
| 5,269,160 | A | 12/1993 | Wood |
| 5,269,783 | A | 12/1993 | Sander |
| 5,269,806 | A | 12/1993 | Sardelis et al. |
| 5,269,809 | A | 12/1993 | Hayhurst et al. |
| 5,279,311 | A | 1/1994 | Snyder |
| 5,281,422 | A | 1/1994 | Badylak et al. |
| 5,282,809 | A | 2/1994 | Kammerer et al. |
| 5,282,832 | A | 2/1994 | Toso et al. |
| 5,282,867 | A | 2/1994 | Mikhail |
| 5,285,040 | A | 2/1994 | Brandberg et al. |
| 5,290,217 | A | 3/1994 | Campos |
| 5,290,243 | A | 3/1994 | Chodorow et al. |
| 5,306,301 | A | 4/1994 | Graf et al. |
| 5,312,410 | A | 5/1994 | Miller et al. |
| 5,312,422 | A | 5/1994 | Trott |
| 5,312,438 | A | 5/1994 | Johnson |
| 5,314,429 | A | 5/1994 | Goble |
| 5,318,566 | A | 6/1994 | Miller |
| 5,318,575 | A | 6/1994 | Chesterfield et al. |
| 5,318,577 | A | 6/1994 | Li |
| 5,318,578 | A | 6/1994 | Hasson |
| 5,320,115 | A | 6/1994 | Kenna |
| 5,320,626 | A | 6/1994 | Schmieding |
| 5,320,633 | A | 6/1994 | Allen et al. |
| 5,324,308 | A | 6/1994 | Pierce |
| 5,330,489 | A | 7/1994 | Green et al. |
| 5,333,625 | A | 8/1994 | Klein |
| 5,334,204 | A | 8/1994 | Clewett et al. |
| 5,336,229 | A | 8/1994 | Noda |
| 5,336,231 | A | 8/1994 | Adair |
| 5,336,240 | A | 8/1994 | Metzler et al. |
| 5,339,870 | A | 8/1994 | Green et al. |

(56) References Cited

U.S. PATENT DOCUMENTS

| | | |
|---|---|---|
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |

(56) References Cited

U.S. PATENT DOCUMENTS

| | | |
|---|---|---|
| 5,603,716 A | 2/1997 | Morgan et al. |
| 5,607,429 A | 3/1997 | Hayano et al. |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A * | 7/1997 | Graf et al. .................. 606/151 |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,581 A | 3/1998 | Br.ang.nemark et al. |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,814,056 A | 9/1998 | Prosst et al. |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |

(56) References Cited

U.S. PATENT DOCUMENTS

| | | |
|---|---|---|
| 5,935,119 A | 8/1999 | Guy et al. |
| 5,935,133 A | 8/1999 | Wagner et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger et al. |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom et al. |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |

(56) References Cited

U.S. PATENT DOCUMENTS

| | | |
|---|---|---|
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 * | 2/2003 | Hein ............... 623/13.13 |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 * | 12/2003 | Morgan et al. ............... 606/232 |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 * | 2/2004 | Skiba .................. 606/232 |

(56) References Cited

U.S. PATENT DOCUMENTS

| | | |
|---|---|---|
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B2 | 2/2007 | Andrews |
| 7,201,722 B2 | 4/2007 | Krueger |
| 7,207,993 B1 | 4/2007 | Baldwin et al. |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,285,124 B2 | 10/2007 | Foerster |
| 7,303,577 B1 | 12/2007 | Dean |
| 7,306,417 B2 | 12/2007 | Dorstewitz |
| 7,309,355 B2 * | 12/2007 | Donnelly et al. ......... 623/13.14 |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,494,506 B2 | 2/2009 | Brulez et al. |
| D587,807 S | 3/2009 | Wolf et al. |
| 7,513,910 B2 | 4/2009 | Buskirk et al. |
| 7,572,298 B2 | 8/2009 | Roller et al. |
| 7,578,825 B2 | 8/2009 | Huebner |
| 7,585,311 B2 | 9/2009 | Green et al. |
| 7,597,705 B2 | 10/2009 | Forsberg et al. |
| 7,601,165 B2 * | 10/2009 | Stone ............................. 606/232 |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 * | 2/2010 | Stone et al. .................... 606/232 |
| 7,670,279 B2 | 3/2010 | Gertner |
| 7,678,123 B2 | 3/2010 | Chanduszko |
| 7,695,493 B2 | 4/2010 | Saadat et al. |
| 7,731,732 B2 | 6/2010 | Ken |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,776,041 B1 | 8/2010 | Walters |
| 7,803,173 B2 | 9/2010 | Burkhart et al. |
| 7,819,895 B2 | 10/2010 | Ginn et al. |
| 7,828,850 B2 | 11/2010 | Cauthen, III et al. |
| 7,857,830 B2 | 12/2010 | Stone et al. |
| 7,867,264 B2 | 1/2011 | McDevitt et al. |
| 7,875,058 B2 | 1/2011 | Holmes, Jr. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |

(56) References Cited

U.S. PATENT DOCUMENTS

| | | | |
|---|---|---|---|
| 8,088,130 B2 | 1/2012 | Kaiser et al. | |
| 8,114,127 B2 | 2/2012 | West, Jr. | |
| 8,114,128 B2 | 2/2012 | Cauldwell et al. | |
| 8,118,835 B2 | 2/2012 | Weisel et al. | |
| 8,118,836 B2* | 2/2012 | Denham et al. | 606/232 |
| 8,128,658 B2* | 3/2012 | Kaiser et al. | 606/232 |
| 8,137,382 B2* | 3/2012 | Denham et al. | 606/232 |
| 8,162,997 B2 | 4/2012 | Struhl | |
| 8,167,906 B2 | 5/2012 | Cauldwell et al. | |
| 8,221,454 B2 | 7/2012 | Schaffhausen | |
| 8,231,654 B2 | 7/2012 | Kaiser et al. | |
| 8,251,998 B2 | 8/2012 | Hoeppner et al. | |
| 8,252,022 B2 | 8/2012 | Holman et al. | |
| 8,273,106 B2 | 9/2012 | Stone et al. | |
| 8,292,921 B2 | 10/2012 | Stone et al. | |
| 8,298,262 B2 | 10/2012 | Stone et al. | |
| 8,303,604 B2 | 11/2012 | Stone et al. | |
| 8,317,825 B2 | 11/2012 | Stone | |
| 8,337,525 B2 | 12/2012 | Stone et al. | |
| 8,343,155 B2 | 1/2013 | Fisher et al. | |
| 8,343,227 B2* | 1/2013 | Metzger et al. | 623/20.31 |
| 8,361,113 B2 | 1/2013 | Stone et al. | |
| 8,409,253 B2 | 4/2013 | Stone et al. | |
| 8,486,114 B2 | 7/2013 | Gillard et al. | |
| 8,500,818 B2* | 8/2013 | Metzger et al. | 623/20.31 |
| 2001/0010005 A1 | 7/2001 | Kammerer et al. | |
| 2001/0014825 A1 | 8/2001 | Burke et al. | |
| 2001/0019649 A1 | 9/2001 | Field et al. | |
| 2001/0029387 A1 | 10/2001 | Wolf et al. | |
| 2001/0037131 A1 | 11/2001 | Schmieding et al. | |
| 2001/0037153 A1 | 11/2001 | Rockwood et al. | |
| 2001/0041916 A1 | 11/2001 | Bonutti | |
| 2001/0041937 A1 | 11/2001 | Rieser et al. | |
| 2001/0041938 A1* | 11/2001 | Hein | 623/13.13 |
| 2001/0044639 A1 | 11/2001 | Levinson | |
| 2001/0047206 A1 | 11/2001 | Sklar et al. | |
| 2001/0051816 A1 | 12/2001 | Enzerink et al. | |
| 2001/0053934 A1 | 12/2001 | Schmieding | |
| 2002/0001964 A1 | 1/2002 | Choi | |
| 2002/0004669 A1 | 1/2002 | Bartlett | |
| 2002/0007182 A1 | 1/2002 | Kim | |
| 2002/0010513 A1 | 1/2002 | Schmieding | |
| 2002/0013607 A1 | 1/2002 | Lemer | |
| 2002/0013608 A1 | 1/2002 | ElAttrache et al. | |
| 2002/0019649 A1 | 2/2002 | Sikora et al. | |
| 2002/0029066 A1 | 3/2002 | Foerster | |
| 2002/0032465 A1 | 3/2002 | Lemer | |
| 2002/0055780 A1 | 5/2002 | Sklar | |
| 2002/0058966 A1 | 5/2002 | Tormala et al. | |
| 2002/0077659 A1 | 6/2002 | Johnson et al. | |
| 2002/0099411 A1 | 7/2002 | Bartlett | |
| 2002/0111653 A1 | 8/2002 | Foerster | |
| 2002/0120270 A1 | 8/2002 | Trieu et al. | |
| 2002/0120292 A1 | 8/2002 | Morgan | |
| 2002/0123752 A1 | 9/2002 | Schultheiss et al. | |
| 2002/0128654 A1 | 9/2002 | Steger et al. | |
| 2002/0128684 A1 | 9/2002 | Foerster | |
| 2002/0129820 A1 | 9/2002 | Ryan et al. | |
| 2002/0143336 A1 | 10/2002 | Hearn | |
| 2002/0147463 A1 | 10/2002 | Martinek | |
| 2002/0161401 A1 | 10/2002 | Steiner | |
| 2002/0161439 A1 | 10/2002 | Strobel et al. | |
| 2002/0165548 A1 | 11/2002 | Jutley | |
| 2002/0165611 A1 | 11/2002 | Enzerink et al. | |
| 2002/0169452 A1 | 11/2002 | Tormala et al. | |
| 2002/0169477 A1 | 11/2002 | Demopulos et al. | |
| 2002/0169478 A1 | 11/2002 | Schwartz et al. | |
| 2002/0173788 A1 | 11/2002 | Bojarski et al. | |
| 2002/0177853 A1 | 11/2002 | Chervitz et al. | |
| 2002/0188298 A1 | 12/2002 | Chan | |
| 2002/0193830 A1 | 12/2002 | Bonutti | |
| 2003/0004545 A1 | 1/2003 | Burkhart et al. | |
| 2003/0023268 A1 | 1/2003 | Lizardi | |
| 2003/0032961 A1 | 2/2003 | Pelo et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0065391 A1 | 4/2003 | Re et al. | |
| 2003/0078585 A1 | 4/2003 | Johnson et al. | |
| 2003/0078603 A1 | 4/2003 | Schaller et al. | |
| 2003/0078617 A1 | 4/2003 | Schwartz et al. | |
| 2003/0083662 A1 | 5/2003 | Middleton | |
| 2003/0083694 A1 | 5/2003 | Miller | |
| 2003/0088251 A1 | 5/2003 | Braun et al. | |
| 2003/0088272 A1 | 5/2003 | Smith | |
| 2003/0105477 A1 | 6/2003 | Schwartz et al. | |
| 2003/0105489 A1 | 6/2003 | Eichhorn et al. | |
| 2003/0120309 A1 | 6/2003 | Colleran et al. | |
| 2003/0130694 A1 | 7/2003 | Bojarski et al. | |
| 2003/0130695 A1 | 7/2003 | McDevitt et al. | |
| 2003/0135214 A1 | 7/2003 | Fetto et al. | |
| 2003/0135239 A1 | 7/2003 | Gabriel et al. | |
| 2003/0135963 A1 | 7/2003 | Holbrook et al. | |
| 2003/0149448 A1 | 8/2003 | Foerster et al. | |
| 2003/0152522 A1 | 8/2003 | Miller et al. | |
| 2003/0153947 A1 | 8/2003 | Koseki | |
| 2003/0167072 A1 | 9/2003 | Oberlander | |
| 2003/0167090 A1 | 9/2003 | Chervitz et al. | |
| 2003/0171811 A1 | 9/2003 | Steiner et al. | |
| 2003/0176865 A1 | 9/2003 | Supinski | |
| 2003/0176919 A1 | 9/2003 | Schmieding | |
| 2003/0176920 A1 | 9/2003 | Sklar et al. | |
| 2003/0181925 A1 | 9/2003 | Bain et al. | |
| 2003/0195528 A1 | 10/2003 | Ritchart | |
| 2003/0195564 A1 | 10/2003 | Tran et al. | |
| 2003/0208210 A1 | 11/2003 | Dreyfuss et al. | |
| 2003/0212456 A1 | 11/2003 | Lipchitz et al. | |
| 2003/0220660 A1 | 11/2003 | Kortenbach et al. | |
| 2003/0225459 A1 | 12/2003 | Hammer et al. | |
| 2003/0229396 A1 | 12/2003 | Andrews | |
| 2004/0002734 A1 | 1/2004 | Fallin et al. | |
| 2004/0006345 A1 | 1/2004 | Vlahos et al. | |
| 2004/0006346 A1 | 1/2004 | Holmen et al. | |
| 2004/0015171 A1 | 1/2004 | Bojarski et al. | |
| 2004/0015172 A1 | 1/2004 | Biedermann et al. | |
| 2004/0024456 A1 | 2/2004 | Brown et al. | |
| 2004/0024457 A1 | 2/2004 | Boyce et al. | |
| 2004/0039389 A1 | 2/2004 | West et al. | |
| 2004/0044391 A1 | 3/2004 | Porter | |
| 2004/0059357 A1 | 3/2004 | Koseki | |
| 2004/0087981 A1 | 5/2004 | Berube et al. | |
| 2004/0092936 A1 | 5/2004 | Miller et al. | |
| 2004/0093031 A1 | 5/2004 | Burkhart et al. | |
| 2004/0093032 A1 | 5/2004 | Sinnott et al. | |
| 2004/0098051 A1 | 5/2004 | Fallin et al. | |
| 2004/0098053 A1 | 5/2004 | Tran | |
| 2004/0111117 A1 | 6/2004 | Colleran et al. | |
| 2004/0122431 A1 | 6/2004 | Biedermann et al. | |
| 2004/0133206 A1 | 7/2004 | Stevens et al. | |
| 2004/0133211 A1 | 7/2004 | Raskin et al. | |
| 2004/0138664 A1 | 7/2004 | Bowman | |
| 2004/0138683 A1 | 7/2004 | Shelton et al. | |
| 2004/0138704 A1 | 7/2004 | Gambale et al. | |
| 2004/0138706 A1 | 7/2004 | Abrams et al. | |
| 2004/0138747 A1 | 7/2004 | Kaladelfos | |
| 2004/0143344 A1 | 7/2004 | Malaviya et al. | |
| 2004/0147932 A1 | 7/2004 | Burkinshaw et al. | |
| 2004/0147958 A1 | 7/2004 | Lam et al. | |
| 2004/0153103 A1 | 8/2004 | Schwartz et al. | |
| 2004/0153153 A1 | 8/2004 | Elson et al. | |
| 2004/0162579 A1 | 8/2004 | Foerster | |
| 2004/0166169 A1 | 8/2004 | Malaviya et al. | |
| 2004/0181234 A1 | 9/2004 | McDevitt et al. | |
| 2004/0182968 A1 | 9/2004 | Gentry | |
| 2004/0187314 A1 | 9/2004 | Johnson | |
| 2004/0193185 A1 | 9/2004 | McBrayer | |
| 2004/0199169 A1 | 10/2004 | Koons et al. | |
| 2004/0204722 A1 | 10/2004 | Sikora et al. | |
| 2004/0220574 A1 | 11/2004 | Pelo et al. | |
| 2004/0225292 A1 | 11/2004 | Sasso et al. | |
| 2004/0225305 A1 | 11/2004 | Ewers et al. | |
| 2004/0236353 A1 | 11/2004 | Bain et al. | |
| 2004/0236373 A1 | 11/2004 | Anspach | |

(56) References Cited

U.S. PATENT DOCUMENTS

| | | |
|---|---|---|
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267361 A1* | 12/2004 | Donnelly et al. .......... 623/13.14 |
| 2004/0267362 A1* | 12/2004 | Hwang et al. .............. 623/13.15 |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1* | 3/2005 | Clark et al. ..................... 606/72 |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0212055 A1 | 9/2006 | Karabey et al. |
| 2006/0229671 A1 | 10/2006 | Steiner et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0282082 A1 | 12/2006 | Fanton et al. |
| 2006/0282083 A1* | 12/2006 | Fanton et al. .................. 606/72 |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |

(56) References Cited

U.S. PATENT DOCUMENTS

| | | |
|---|---|---|
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225719 A1* | 9/2007 | Stone et al. ................ 606/72 |
| 2007/0225805 A1 | 9/2007 | Schmieding |
| 2007/0233241 A1* | 10/2007 | Graf et al. ............. 623/13.14 |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2008/0027430 A1 | 1/2008 | Montgomery et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0097430 A1 | 4/2008 | Bernstein et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0300611 A1 | 12/2008 | Houser et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0046733 A1* | 2/2011 | Eggli ................. 623/13.14 |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'Oca |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0089193 A1 | 4/2012 | Stone et al. |
| 2012/0095470 A1 | 4/2012 | Kaiser et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0245585 A1 | 9/2012 | Kaiser et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0103082 A1 | 4/2013 | Kaiser et al. |
| 2013/0110251 A1 | 5/2013 | Metzger et al. |
| 2013/0116730 A1 | 5/2013 | Denham et al. |
| 2013/0123813 A1 | 5/2013 | Stone et al. |
| 2013/0274812 A1 | 10/2013 | Dell'Oca |
| 2013/0289564 A1 | 10/2013 | Bernstein et al. |
| 2014/0046367 A1 | 2/2014 | Stone et al. |
| 2014/0046368 A1 | 2/2014 | Kaiser et al. |

(56) References Cited

U.S. PATENT DOCUMENTS

| | | | |
|---|---|---|---|
| 2014/0067081 A1 | 3/2014 | Stone | |
| 2014/0088655 A1 | 3/2014 | Stone et al. | |
| 2014/0094913 A1 | 4/2014 | Berelsman et al. | |

FOREIGN PATENT DOCUMENTS

| | | | |
|---|---|---|---|
| AU | 5850469 | | 1/1971 |
| AU | 5963869 | | 2/1971 |
| AU | 1505470 | | 11/1971 |
| AU | 2223767 | | 5/1973 |
| AU | 3615171 | | 5/1973 |
| AU | 5028569 | | 9/1973 |
| AU | 7110887 | | 10/1987 |
| AU | 639410 | | 11/1989 |
| AU | 651929 | | 8/1994 |
| DE | 2529669 | | 3/1976 |
| DE | 2747312 | | 4/1979 |
| DE | 2818254 | | 10/1979 |
| DE | 2919009 | | 11/1979 |
| DE | 3027138 | | 12/1981 |
| DE | 3225620 | | 2/1983 |
| DE | 3136083 | | 3/1983 |
| DE | 233303 | | 2/1986 |
| DE | 4127550 | | 2/1993 |
| DE | 4302397 | | 7/1993 |
| DE | 29621340 | | 5/1998 |
| DE | 19841252 | | 3/2000 |
| EP | 19062 | A1 | 11/1980 |
| EP | 0108912 | | 5/1984 |
| EP | 0129442 | | 12/1984 |
| EP | 0172130 | | 2/1986 |
| EP | 0241240 | | 10/1987 |
| EP | 0241792 | | 10/1987 |
| EP | 0260970 | | 3/1988 |
| EP | 0270704 | | 6/1988 |
| EP | 0282789 | | 9/1988 |
| EP | 0315371 | | 5/1989 |
| EP | 0317406 | | 5/1989 |
| EP | 0340159 | | 11/1989 |
| EP | 0346183 | | 12/1989 |
| EP | 0349173 | | 1/1990 |
| EP | 0374088 | | 6/1990 |
| EP | 0409364 | | 1/1991 |
| EP | 0415915 | | 3/1991 |
| EP | 0440991 | | 8/1991 |
| EP | 440991 | A1 * | 8/1991 ............. A61B 17/16 |
| EP | 0441065 | | 8/1991 |
| EP | 0451932 | | 10/1991 |
| EP | 0464480 | | 1/1992 |
| EP | 0497079 | | 8/1992 |
| EP | 0502509 | | 9/1992 |
| EP | 0502698 | | 9/1992 |
| EP | 520177 | | 12/1992 |
| EP | 0546726 | | 6/1993 |
| EP | 0574707 | | 12/1993 |
| EP | 0582514 | | 2/1994 |
| EP | 0591991 | | 4/1994 |
| EP | 0598219 | | 5/1994 |
| EP | 0611551 A1 | | 8/1994 |
| EP | 0627203 | | 12/1994 |
| EP | 0651979 | | 5/1995 |
| EP | 0669110 | | 8/1995 |
| EP | 0686373 | | 12/1995 |
| EP | 0702933 | | 3/1996 |
| EP | 0775473 | | 5/1997 |
| EP | 0913123 | | 5/1999 |
| EP | 0913131 | | 5/1999 |
| EP | 99121106 | | 10/1999 |
| EP | 991210527 | | 10/1999 |
| EP | 0995409 | | 4/2000 |
| EP | 1013229 | | 6/2000 |
| EP | 1093773 | | 4/2001 |
| EP | 1093774 | | 4/2001 |
| EP | 1555945 | | 7/2005 |
| EP | 2238944 A2 | | 10/2010 |
| EP | 2544607 A1 | | 1/2013 |
| EP | 2709557 A1 | | 3/2014 |
| FR | 2622790 | | 5/1989 |
| FR | 2655840 | | 6/1991 |
| FR | 2682867 | | 4/1993 |
| FR | 2687911 | | 9/1993 |
| FR | 2688689 | | 9/1993 |
| FR | 2704140 | | 10/1994 |
| FR | 2717070 | | 9/1995 |
| FR | 2723528 | | 2/1996 |
| FR | 2744010 | | 8/1997 |
| FR | 2745999 | | 9/1997 |
| FR | 2770764 | | 5/1999 |
| GB | 401677 | | 11/1933 |
| GB | 1413477 | | 11/1975 |
| GB | 1485681 | | 9/1977 |
| GB | 2083751 | | 3/1982 |
| GB | 2118474 | | 11/1983 |
| GB | 2227175 | | 7/1990 |
| GB | 2253147 A | | 9/1992 |
| GB | 2312376 | | 10/1997 |
| GB | 2403416 A | | 1/2005 |
| JP | 5362911 | | 5/1978 |
| JP | 5362912 | | 5/1978 |
| JP | 5374942 | | 6/1978 |
| JP | 5378230 | | 6/1978 |
| JP | 62159647 | | 7/1987 |
| JP | 62295657 | | 12/1987 |
| JP | 5269160 | | 10/1993 |
| JP | 5300917 | | 11/1993 |
| JP | 751292 | | 2/1995 |
| JP | 10211213 | | 8/1998 |
| WO | WO-8300615 | | 3/1983 |
| WO | WO-8603666 | | 7/1986 |
| WO | WO-8701270 | | 3/1987 |
| WO | WO-8901767 | | 3/1989 |
| WO | WO-8909030 | | 10/1989 |
| WO | WO-8910096 | | 11/1989 |
| WO | WO-9008510 | | 8/1990 |
| WO | WO-9203980 | | 3/1992 |
| WO | WO-9314705 | | 8/1993 |
| WO | WO-9315694 | | 8/1993 |
| WO | WO-9502373 | | 1/1995 |
| WO | WO-9503003 | | 2/1995 |
| WO | WO-9529637 | | 11/1995 |
| WO | WO-9532670 | | 12/1995 |
| WO | WO-9609797 A1 | | 4/1996 |
| WO | WO-9629029 | | 9/1996 |
| WO | WO-9737603 | | 10/1997 |
| WO | WO-9812991 | | 4/1998 |
| WO | WO-9812992 | | 4/1998 |
| WO | WO-9822047 | | 5/1998 |
| WO | WO-9822048 | | 5/1998 |
| WO | WO-9901084 | | 1/1999 |
| WO | WO-9912480 | | 3/1999 |
| WO | WO-9937219 A1 | | 7/1999 |
| WO | WO-9944544 | | 9/1999 |
| WO | WO-9952472 A1 | | 10/1999 |
| WO | WO-0040159 | | 7/2000 |
| WO | WO-0139671 | | 6/2001 |
| WO | WO-0236020 | | 5/2002 |
| WO | WO-03005914 A1 | | 1/2003 |
| WO | WO-03071962 | | 9/2003 |
| WO | WO-03077772 | | 9/2003 |
| WO | WO-03092551 A1 | | 11/2003 |
| WO | WO-2004091412 A1 | | 10/2004 |
| WO | WO-2005104992 A1 | | 11/2005 |
| WO | WO-2006023661 A2 | | 3/2006 |
| WO | WO-2006055823 A2 | | 5/2006 |
| WO | WO-2007045460 A2 | | 4/2007 |
| WO | WO-2007109280 A2 | | 9/2007 |
| WO | WO-2008002550 A2 | | 1/2008 |
| WO | WO-2008015171 A1 | | 2/2008 |
| WO | WO-2008073588 A2 | | 6/2008 |
| WO | WO-2009012021 A1 | | 1/2009 |
| WO | WO-2011112371 A1 | | 9/2011 |

(56) References Cited

FOREIGN PATENT DOCUMENTS

| WO | WO-2011150238 A1 | 12/2011 |
|---|---|---|
| WO | WO-2012134999 A1 | 10/2012 |
| WO | WO-2012158583 A1 | 11/2012 |

OTHER PUBLICATIONS

"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
"Arthroscopic Meniscal Repair using the Meniscal Cinch™", Surgical Technique brochure. (2008) Arthrex® 6 sheets.
Pioneer® Sternal Cable System (2010).
Rapid Sternal Closure (2006) KLS Martin L.P. http://www.rapidsternalclosure.com/medical/demo.php Web accessed Sep. 8, 2008.
Saxena, Pankaj, MCh, DNB et al., "Use of Double Wires in Sternal Closure, A Useful Technique," Texas Heart® Institute. Journal List>Tex Heart Inst J > v.33(4); (2006).
Zeitani, Jacob, M.D., "A New Sternal Reinforcement Device to Prevent and Treat Sternal Dehiscence," CTSNet.org (Jun. 30, 2008).
US 6,238,418, 5/2001, Schwartz et al. (withdrawn).
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Sure fire Hybrid Meniscal Device; Launch Date: Fall AANA 2004.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Invitation to Pay Additional Fees mailed Jul. 19, 2012, for PCT/US2012/037703 claiming benefit of U.S. Appl. No. 13/109,667, filed May 7, 2011.
"Suture Tensioner w/Tensiometer," Arthrex® , Inc. catalog "Next Generation in Knee Ligament Reconstruction & Repair Technology," 2009.
"TriTis™ Tibial Fixation System and Implant" brochure. Scandius Biomedical (2006).
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
International Preliminary Report on Patentability mailed Sep. 20, 2012 for PCT/US2011/026349 which claims benefit of U.S. Appl. No. 12/719,337, filed Mar. 8, 2010.
International Preliminary Report on Patentability mailed Dec. 6, 2012 for PCT/US2011/038188 claiming benefit of U.S. Appl. No. 12/788,966, filed May 27, 2010.
International Preliminary Report on Patentability and Written Opinion mailed Nov. 28, 2013 for PCT/US2012/037703, which claims benefit of U.S. Appl. No. 13/109,672, filed May 17, 2011,and U.S. Appl. No. 13/109,667, filed May 17, 2011.
International Search Report and Written Opinion mailed Mar. 6, 2014 for PCT/US2013/075989 which claims benefit of U.S. Appl. No. 13/720,648, filed Dec. 19, 2012.

* cited by examiner

FIG 3
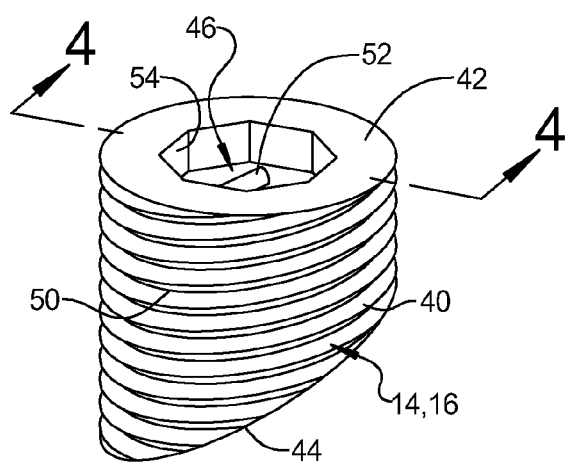
FIG 4
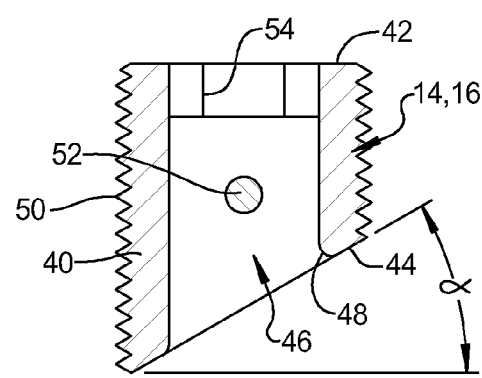
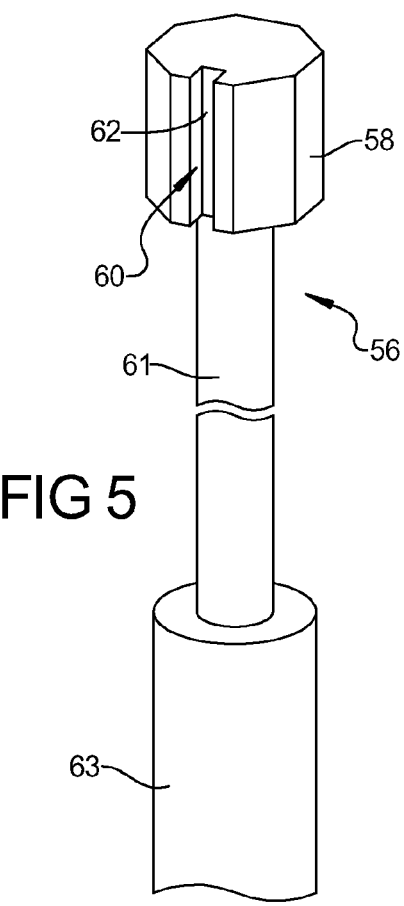
FIG 5
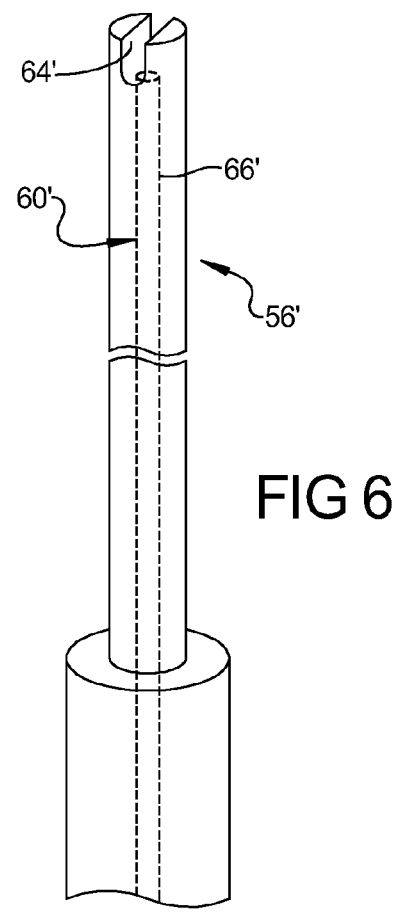
FIG 6

PROSTHETIC LIGAMENT SYSTEM FOR KNEE JOINT

CROSS REFERENCE TO RELATED APPLICATION

This application is a continuation-in-part of U.S. patent application Ser. No. 12/489,168 filed on Jun. 22, 2009, which is a continuation-in-part of U.S. patent application Ser. No. 12/474,802 filed on May 29, 2009 and is now U.S. Pat. No. 8,088,130, issued Jan. 3, 2012, which is a continuation-in-part of (a) U.S. patent application Ser. No. 12/196,405 filed on Aug. 22, 2008, and is now U.S. Pat. No. 8,128,658, issued Mar. 6, 2012; (b) U.S. patent application Ser. No. 12/196,407 filed on Aug. 22, 2008, and is now U.S. Pat. No. 8,137,382, issued on Mar. 20, 2012; (c) U.S. patent application Ser. No. 12/196,410 filed on Aug. 22, 2008, and is now U.S. Pat. No. 8,118,836, issued on Feb. 21, 2012; and (d) a continuation-in-part of U.S. patent application Ser. No. 11/541,506 filed on Sep. 29, 2006, which is now U.S. Pat. No. 7,601,165 issued on Oct. 13, 2009.

This application is a continuation-in-part of U.S. patent application Ser. No. 12/570,854 filed on Sep. 30, 2009, which is a continuation-in-part of (a) U.S. patent application Ser. No. 12/014,399 filed on Jan. 15, 2008 and is now U.S. Pat. No. 7,909,851, issued on Mar. 22, 2011; and (b) U.S. patent application Ser. No. 12/014,340 filed on Jan. 15, 2008 and is now U.S. Pat. No. 7,905,904, issued on Mar. 15, 2011.

This application is a continuation-in-part of U.S. patent application Ser. No. 12/702,067 filed on Feb. 8, 2010, which is a continuation of U.S. patent application Ser. No. 11/541,505 filed on Sep. 29, 2006 and is now U.S. Pat. No. 7,658,751 issued on Feb. 9, 2010.

This application is a continuation-in-part of U.S. patent application Ser. No. 12/196,398 filed Aug. 22, 2008 and is now U.S. Pat. No. 7,959,650, issued on Jun. 14, 2011; which is a continuation-in-part of U.S. patent application Ser. No. 11/784,821 filed Apr. 10, 2007.

The disclosures of all the above applications are incorporated by reference herein.

FIELD

The following relates to a knee joint and, more particularly, relates to a prosthetic ligament system for a knee joint.

BACKGROUND

The statements in this section merely provide background information related to the present disclosure and may not constitute prior art.

Articulating anatomical skeletal joints, such as knee joints include a plurality of ligaments, such as an anterior cruciate ligament (ACL). The ligaments extend between and connect the bones of the knee joint. In some cases, trauma or wear of the knee joint can necessitate replacement and/or repair of the ligament(s).

Conventional prosthetic ligaments for the knee, for example, can be made out of a graft of biological material (e.g., an autograft, allograft, xenograft, or artificial graft). These grafts are typically attached to the bones with a fastener (e.g., a bone screw, etc.) that is fixed to bone.

The following disclosure relates to a prosthetic ligament system that supports and restores normal movement of a knee joint. The prosthetic ligament system of the present disclosure can be quickly and conveniently implanted.

SUMMARY

A system for a knee joint with a tibia and a femur is disclosed. The system includes a first fastener operable to be connected to the tibia. The system also includes a second fastener operable to be connected to the femur. Furthermore, the system includes a prosthetic ligament member that is flexible. The ligament member is operably coupled to both the first and second fasteners to support the tibia and the femur for relative movement. The ligament member extends from a first end to a second end. The ligament member also includes an outer wall that defines a hollow longitudinal passage portion. The first end extends into the longitudinal passage portion through the outer wall and out of the longitudinal passage through the outer wall to define a first adjustable loop, and the second end extends into the longitudinal passage portion through the outer wall and out of the longitudinal passage portion through the outer wall to define a second adjustable loop. At least one of the first and second adjustable loops receives at least one of the first and second fasteners.

A method of repairing a knee joint is also disclosed. The method includes operably coupling a first fastener to a tibia of a patient and operably coupling a second fastener to a femur of a patient. The method further includes intraoperatively adjusting a tension of a prosthetic ligament member that is flexible and that is operatively coupled to both the first and second fasteners. The ligament member has a first end, a second end, and an outer wall that defines a hollow longitudinal passage portion. The first end extends into the longitudinal passage portion through outer wall and out of the longitudinal passage portion through the outer wall to define a first adjustable loop and a first free end. Also, the second end extends into the longitudinal passage portion through the outer wall and out of the longitudinal passage portion through the outer wall to define a second adjustable loop and a second free end.

Still further, a system for a knee joint with a tibia and a femur is disclosed. This system includes a first fastener connected to the tibia and a second fastener connected to the femur. Furthermore, the system includes a prosthetic ligament member that is flexible and that is operably coupled to both the first and second fasteners to support the tibia and the femur for relative movement. The ligament member extends from a first end to a second end, and the ligament member includes an outer wall that defines a hollow longitudinal passage portion. At least one first aperture extends through the outer wall and is disposed between the first and second ends, and at least one second aperture also extends through the outer wall and is disposed between the first and second ends. The first end extends through the at least one first aperture and the at least one second aperture and the longitudinal passage portion to define a first adjustable loop and a first free end. Also, the second end extends through the at least one first aperture and the at least one second aperture and the longitudinal passage portion to define a second adjustable loop and a second free end. At least one of the first and second adjustable loops receives at least one of the first and second fasteners. Moreover, the first and second free ends are pullable to increase a tension in the ligament member. The ligament member includes a plurality of braided fibers made from at least one of polyethylene, polyester, polyetheretherketone (PEEK), poly-para-phenylene terephthalamide, collagen, polyglycolic acid (PGA), polylactic acid (PLA), polyurethane urea, and silk.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 3 is a perspective view of a fastener of the system of FIG. 1;

FIG. 4 is a section view of the fastener of FIG. 3 taken along the line 4-4 of FIG. 3;

FIG. 5 is a perspective view of an installation tool of the system of FIG. 1;

FIG. 6 is a perspective view of an installation tool of the system of FIG. 1 according to various additional embodiments;

DETAILED DESCRIPTION

Figure 1:
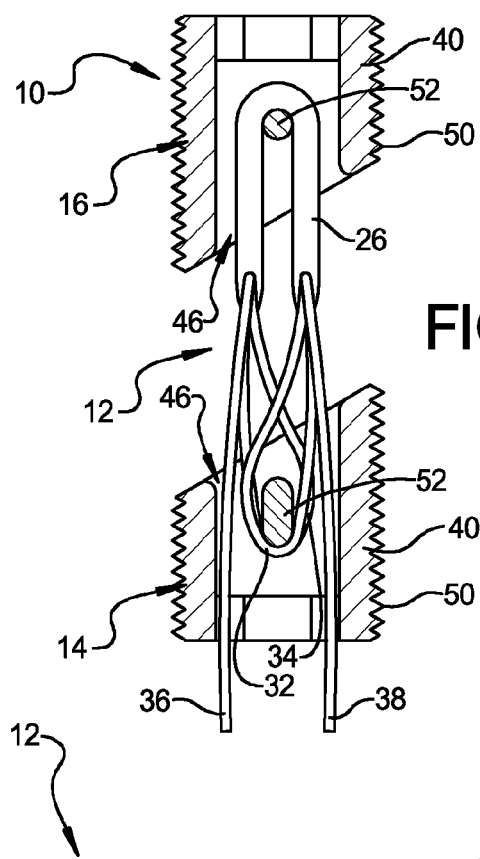
FIG. 1 is a side view, partially in section, of a prosthetic ligament system according to various teachings of the present disclosure.

The following description is merely exemplary in nature and is not intended to limit the present disclosure, application, or uses. It should be understood that throughout the drawings, corresponding reference numerals indicate like or corresponding parts and features.

Referring initially to FIG. 1, a system 10 for repairing a knee joint is disclosed. For instance, the system 10 can be used for repairing an anterior cruciate ligament (ACL) in some embodiments described in greater detail below. However, it will be appreciated that the system 10 can also be used for repairing any other feature of the knee joint (e.g., repair of a medial or lateral ligament of the knee joint) without departing from the scope of the present disclosure. Additionally, it will be appreciated that the system 10 can be used for repairing ligaments of the foot, ankle, hand, wrist, spine, etc. without departing from the scope of the present disclosure.

Figure 8:
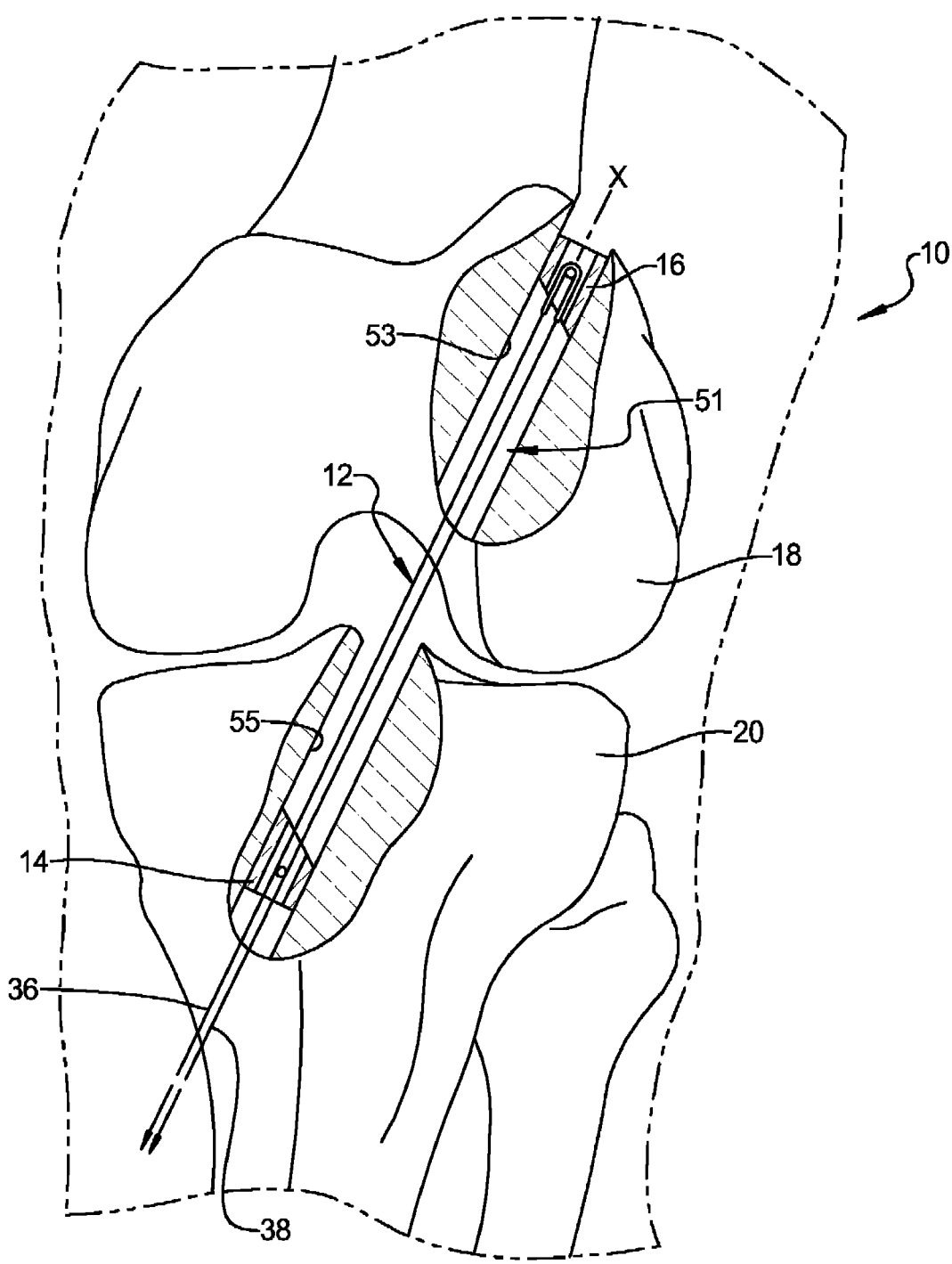
FIG. 8 is a section view of a knee joint during implantation of the system of FIG. 1, wherein the prosthetic ligament member thereof has high tension.

The system 10 can generally include a prosthetic ligament member 12, a first fastener 14, and a second fastener 16. As shown in FIG. 8, and as will be discussed in greater detail, the system 10 can be used, for example, for repairing and/or restoring normal movement of a knee joint to approximate such movement as naturally constrained by anatomical ligaments. More specifically, the first fastener 14 is operable to be connected to a tibia 20 (FIG. 8), and the second fastener 16 is operable to be connected to a femur 18 (FIG. 8). The prosthetic ligament member 12 can be operably coupled to both the first and second fasteners 14, 16 to support the tibia 20 and the femur 18 for relative movement, as will be discussed in greater detail below.

Figure 2A:
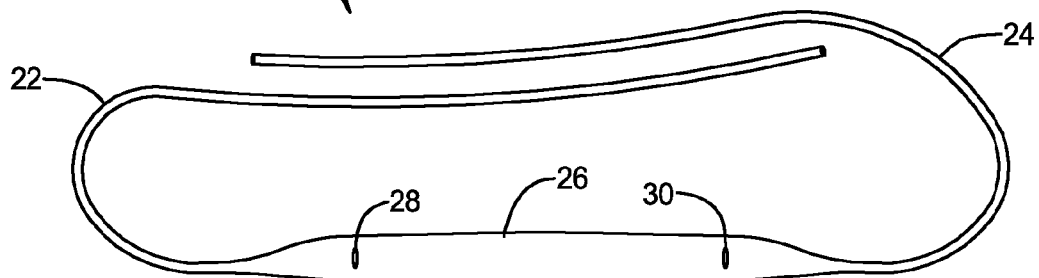
FIG. 2A is a top view of a prosthetic ligament member of the system of FIG. 1 shown in an unlooped state.

The prosthetic ligament member 12 can be formed according to Applicants' co-pending U.S. Patent Application Publication No. 2009/0318961, filed Jun. 22, 2009, which is hereby incorporated by reference in its entirety. More specifically, as shown in FIG. 2A, the ligament member 12 can be elongate and flexible and can extend from a first end 22 to a second end 24. The ligament member 12 can include an outer wall 23 that defines a hollow longitudinal passage portion 26, which is disposed between the first and second ends 22, 24. Moreover, the ligament member 12 can include at least one first aperture 28 that extends through the outer wall 23 and that is disposed between the first and second ends 22, 24. Furthermore, the ligament member 12 can include at least one second aperture 30 that extends through the outer wall 23 and that is disposed between the first and second ends 22, 24. More specifically, the first aperture 28 can be disposed adjacent the first end 22, and the second aperture 30 can be disposed adjacent the second end 24. In the embodiment illustrated, the ligament member 12 can include a single first aperture 28 and a single second aperture 30; however, it will be appreciated that the ligament member 12 can include a plurality of first apertures 28 and a plurality of second apertures 30. As discussed below, the first and second apertures 28, 30 can allow access into or out of the longitudinal passage portion 26 (i.e., entrance into and/or exit from the longitudinal passage portion 26).

Figure 2B:
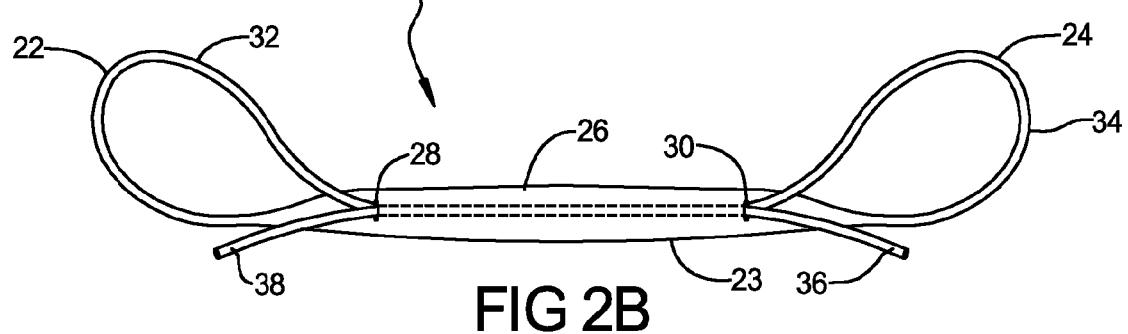
FIG. 2B is a top view of the prosthetic ligament member of the system of FIG. 1 shown in a looped state.

As shown in the embodiment of FIG. 2B, the first end 22 of the ligament member 12 can extend through outer wall 23 via the first aperture 28 to enter the longitudinal passage portion 26, and the first end 22 can exit out of the longitudinal passage portion 26 through the outer wall 23 via the second aperture 30. Likewise, the second end 24 can extend through the outer wall 23 via the second aperture 30 to enter the longitudinal passage portion 26, and the second end 24 can exit out of the longitudinal passage portion 26 through the outer wall 23 via the first aperture 28. It will be appreciated that the first end 22 can enter the longitudinal passage portion 26 through the same aperture (i.e., the first aperture 28) that the second end 24 exits the longitudinal passage portion 26, and the second end 24 can enter the longitudinal passage portion 26 through the same aperture (i.e., the second aperture 30) that the first end 22 exits the longitudinal passage portion 26. As such, the first end 22 can define a first adjustable loop 32 and a first free end 36. Likewise, the second end 24 can define a second adjustable loop 34 and a second free end 38.

Furthermore, it will be appreciated that the first free end 36 can be pulled away from the longitudinal passage portion 26 to thereby reduce the size of the first adjustable loop 32. Likewise, the second free end 38 can be pulled away from the longitudinal passage portion 26 to reduce the size of the second adjustable loop 34.

Figure 2C:
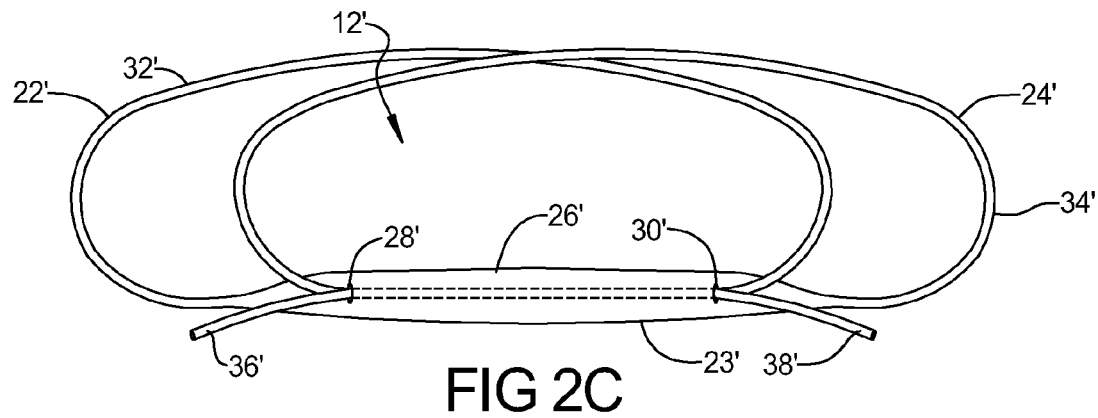
FIG. 2C is a top view of the prosthetic ligament member of the system of FIG. 1 according to additional exemplary embodiments.

It will be appreciated that the ligament member 12 can be configured differently, and the first and second adjustable loops 32, 34 can be formed in any suitable manner. For instance, as shown in FIG. 2C, the first end 22' can extend into the longitudinal passage portion 26' through the second aperture 30' and can extend out of the longitudinal passage portion 26' through the first aperture 28'. More over, the second end 24' can extend into the longitudinal passage portion 26' through the first aperture 28' and out of the longitudinal passage portion 26' through the second aperture 30'.

Figure 2D:
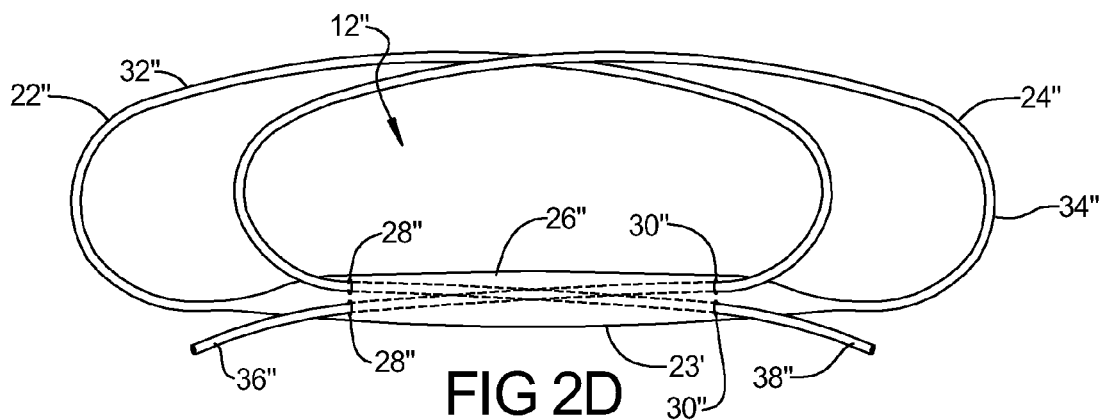
FIG. 2D is a top view of the prosthetic ligament member of the system of FIG. 1 according to additional exemplary embodiments.

Also, as shown in FIG. 2D, the ligament member 12" can include a plurality of first apertures 28" and a plurality of second apertures 30". For instance, the ligament member 12" can include two first apertures 28" and two second apertures 30". Also, the first apertures 28" and second apertures 30" can be spaced apart on opposite sides of the longitudinal axis of the ligament member 12". As shown, the first end 22" can enter the longitudinal passage portion 26" through one of the second apertures 30" and can exit the longitudinal passage portion 26" through one of the first apertures 28". Also, the second end 24" can enter and exit the longitudinal passage portion 26" through different ones of the first and second apertures 28", 30" respectively. As such, the first end 22" enters the longitudinal passage portion 26" through a different aperture 30" from which the second end 24" exits the longitudinal passage portion 26", and the second end 24" enters the longitudinal passage portion 26" through a different aperture 28" from which the first end 22" exits the longitudinal passage portion 26".

It will be appreciated that the ligament member 12, 12', 12" can include any suitable number of adjustable loops 32, 32', 32", 34, 34', 34" by extending into and out of the longitudinal passage portion 26, 26', 26" any suitable number of times. Also, it will be appreciated that the ligament member 12, 12', 12" can include any suitable number of apertures 28, 28', 28", 30, 30', 30". Moreover, the apertures 28, 28', 28", 30, 30', 30" can be disposed in any suitable location on the ligament member 12, 12', 12" (e.g., disposed in alignment along the longitudinal axis of the ligament member 12, 12', 12".

For purposes of discussion, the system 10 will be discussed largely in relation to the embodiments of the ligament member 12 illustrated in FIG. 2B. However, it will be appreciated that the system 10 can similarly incorporate any of the embodiments of the ligament member 12, 12', 12" shown in FIGS. 2B-2D or any other suitable ligament member 12, 12', 12" without departing from the scope of the present disclosure.

As shown in FIG. 1, at least one of the first and second adjustable loops 32, 34 can receive at least one of the first and second fasteners 14, 16 of the system 10. Specifically, as shown in FIG. 1, both the first and second adjustable loops 32, 34 can encircle a portion of the first fastener 14, and the longitudinal passage portion 26 can be folded over a portion of the second fastener 16. However, it will be appreciated that the ligament member 12 can be coupled in any suitable manner to both the first and second fasteners 14, 16 (e.g., first loop 32 encircling the first fastener 14 and the second loop 34 encircling the second fastener 16). By pulling on the first and/or second free ends 36, 38, tension within the first and second adjustable loops 32, 34 and longitudinal passage portion 26 of the ligament member 12 can be adjusted (i.e., increased), and the first and second fasteners 14, 16 will be urged towards each other. In addition, friction between the first and second free ends 36, 38 and the inner surface of the longitudinal passage portion 26 can generally inhibit or lock, in a knotless fashion, the first and second free ends 36, 38 from being pulled back toward the longitudinal passage portion 26, thereby maintaining the desired tension in the ligament member 12.

It will be appreciated that if the ligament member 12' of FIG. 2C is used, both the first and second adjustable loops 32', 34' can encircle the first fastener 14, and the longitudinal passage portion 26' can be folded over the second fastener 16 as described above with relation to the embodiment of FIG. 2B. However, it will be appreciated that the ligament member 12' can be coupled in any suitable manner to both the first and second fasteners 14, 16 (e.g., first loop 32' encircling the first fastener 14 and the second loop 34' encircling the second fastener 16). Furthermore, it will be appreciated that the ligament member 12" of FIG. 2D can be coupled to the fasteners 14, 16 in any of these ways.

The prosthetic ligament member 12 can be made out of any suitable material and can be manufactured in any suitable fashion. For instance, the ligament member 12 can be made out of a flexible and biocompatible material. More specifically, the ligament member 12 can be made out of and/or can include fibers of polyethylene, gel-spun polyethylene, polyester, polyetheretherketone (PEEK), poly-para-phenylene terephthalamide, polycaprolactone, Kevlar, carbon, collagen, polyglycolic acid (PGA), polylactic acid (PLA), polyurethane urea, and/or silk (silk from a silk worm or silk from a spider). In some embodiments, the ligament member 12 can be made out of SERICA material, which is commercially available from SERICA Technologies, Inc. of Medford, Mass. Moreover, in some embodiments, the ligament member 12 can be made out of SPIDREX material, which is commercially available from Neurotex Ltd. In addition, the ligament member 12 can be made out of a material that is injected with a natural and/or artificial collagen. Furthermore, the ligament member 12 can be made out of a partially resorbable material. Additionally, the ligament member 12 can be made out of a material that is treated with a platelet concentration to promote tissue growth. Also, the ligament member 12 can be made out of a material that is easily cuttable with a conventional blade or sharpened edge, once a desired tension is reached in the ligament member 12.

Figure 16:
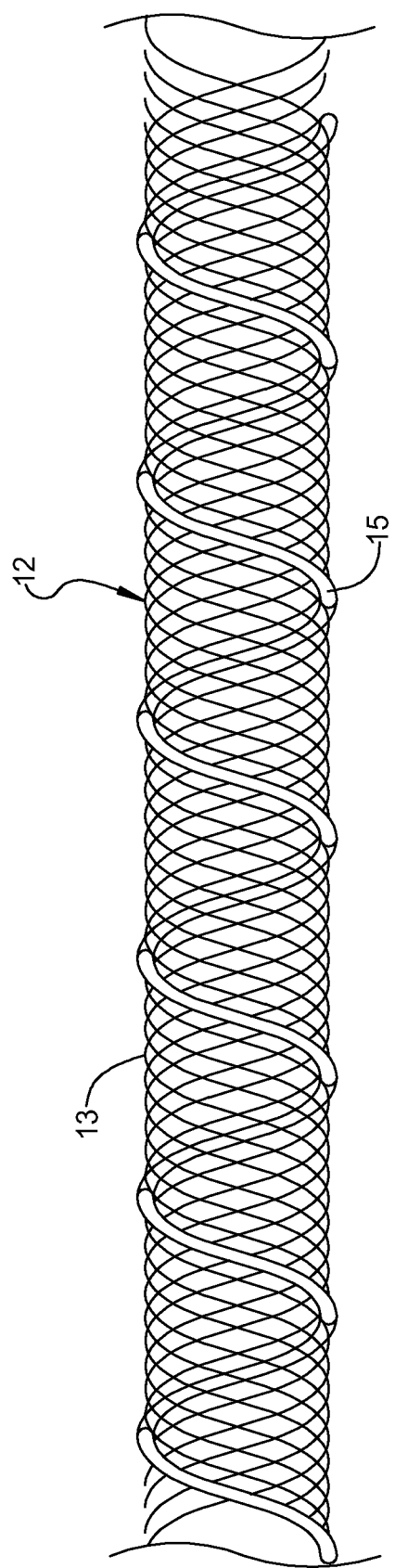
FIG. 16 is a detail view of the prosthetic ligament member of FIGS. 2A through 2D showing different fibers thereof braided together.

Still further, as shown in FIG. 16, the ligament member 12 can be a braided construct made out of a plurality of different fibers 13, 15 that are braided together to form a hollow tube. The fibers 13, 15 can vary in any of a variety of characteristics. For instance, the second fibers 15 can have a greater diameter than that of the first fibers 13 such that the second fibers 15 protrude from the first fibers 13 and such that the second fibers 15 increase the coefficient of friction of the ligament member 12. Furthermore, the first and second fibers 13, 15 can be made out of or include different materials. Additionally, the first fibers 13 be resiliently extendable in a longitudinal direction, whereas the second fibers 15 can be less resiliently extendable and can have a higher tensile strength (i.e., load-bearing capability). Moreover, the first fibers 13 can be a relatively high-strength fiber with a fixed length (i.e., non-resilient) while the second fibers 15 can be constructed so as to promote tissue growth (e.g., serve as a support for tissue regeneration, etc.). It will be appreciated, however, that the ligament member 12 can include a plurality of the same type of fibers without departing from the scope of the present disclosure. Furthermore, it will be appreciated that the ligament member 12 can have any number of fibers, and those fibers can differ in any suitable fashion.

In some embodiments shown in FIG. 16, the first and second fibers 13, 15 can be wrapped around the longitudinal axis of the ligament member 12. Also, in some embodiments, the first and second fibers 13, 15 can be arranged in a fixed sequence along the longitudinal axis. For instance, the first and second fibers 13, 15 can alternate in a one-to-one arrangement along the longitudinal axis, or the first and second fibers 13, 15 can be arranged at fixed intervals along the axis.

Figure 17:
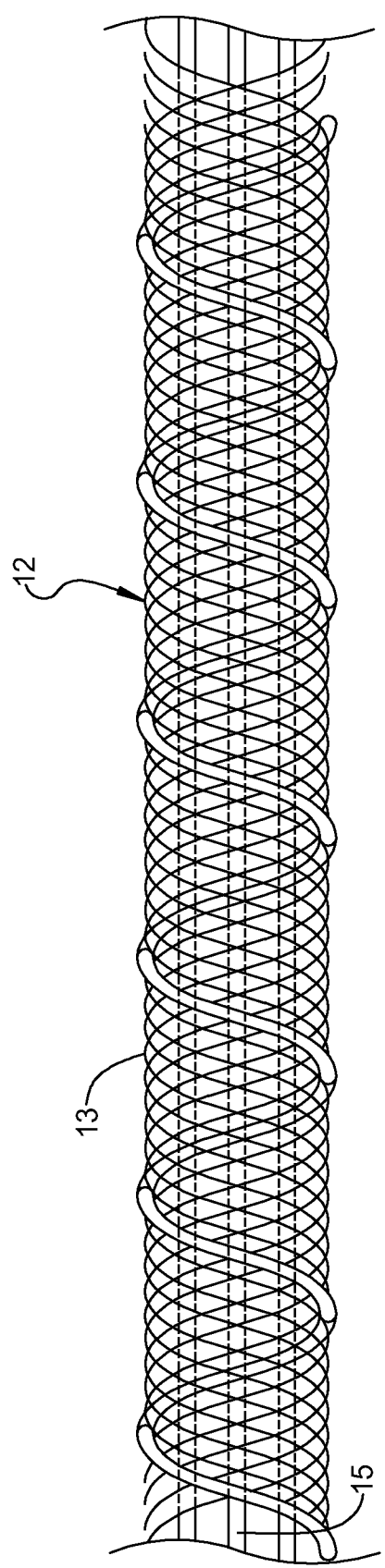
FIG. 17 is a detail view of the prosthetic ligament member of FIGS. 2A through 2D according to various additional exemplary embodiments.

Additionally, in the embodiments of FIG. 17, the second fibers 15 can be arranged substantially parallel to the longitudinal axis of the ligament member 12. Also, the first fibers 13 are wrapped helically about the second fibers 15.

Moreover, the ligament member 12 can be specifically configured for the particular application of the ligament member 12 within the knee joint. For instance, the braiding pattern, the materials, the dimensions, and/or other features of the ligament member 12 can be adapted according to the desired level of tension, the desired load carrying capacity, the desired elasticity (e.g., to simulate the elasticity of natural ligament, the dimensions of the knee joint, etc. In addition, the ligament member 12 can incorporate one or more of the features disclosed in U.S. Patent Publication No. 2005/0119696, filed Feb. 23, 2004 by Walters et al., which is hereby incorporated by reference in its entirety.

Also, the ligament member 12 can be manufactured and configured to include the first and second loops 32, 34 as shown in FIG. 2B before surgery. Because the adjustable loop members 32, 34 are already formed, the surgeon can implant the ligament member 12 into the knee joint without having to construct the loops 32, 34. Furthermore, because of the frictionally self-containing characteristic of the looped ligament member 12, the surgeon need not tie any knots. Accordingly, the ligament member 12 greatly facilitates repair and reconstruction of the knee joint. Also, the ligament member 12 can be relatively compact and can facilitate arthroscopic knee surgery.

Referring now to FIGS. 1, 3, and 4, the fasteners 14, 16 will be discussed in greater detail. For purposes of discussion, it will be assumed that both fasteners 14, 16 are substantially similar. Thus, the following discussion of the fasteners 14, 16 will apply to both of the fasteners 14, 16. However, it will be appreciated that the fasteners 14, 16 could have different features without departing from the scope of the present disclosure.

As shown in FIGS. 3 and 4, the fasteners 14, 16 can include a cylindrical base 40 having a first end 42 and a second end 44. The base 40 can be hollow to define an interior space 46 therein. The ends 42, 44 can be open to the interior space 46. In some embodiments, the second end 44 can be disposed at an angle, α, relative to the first end 42 (FIG. 4). Moreover, the interior portion of the second end 44 can include a fillet 48 (FIG. 4). As will be discussed, the angle, a, and the fillet 48 of the second end 44 can reduce the likelihood of the fastener 14, 16 abrading the ligament member 12, thereby reducing the likelihood of wear of the ligament member 12. Also, the angle, α, can reduce the likelihood of the fastener 14, 16 intruding into the intra-articular space.

Figure 7:
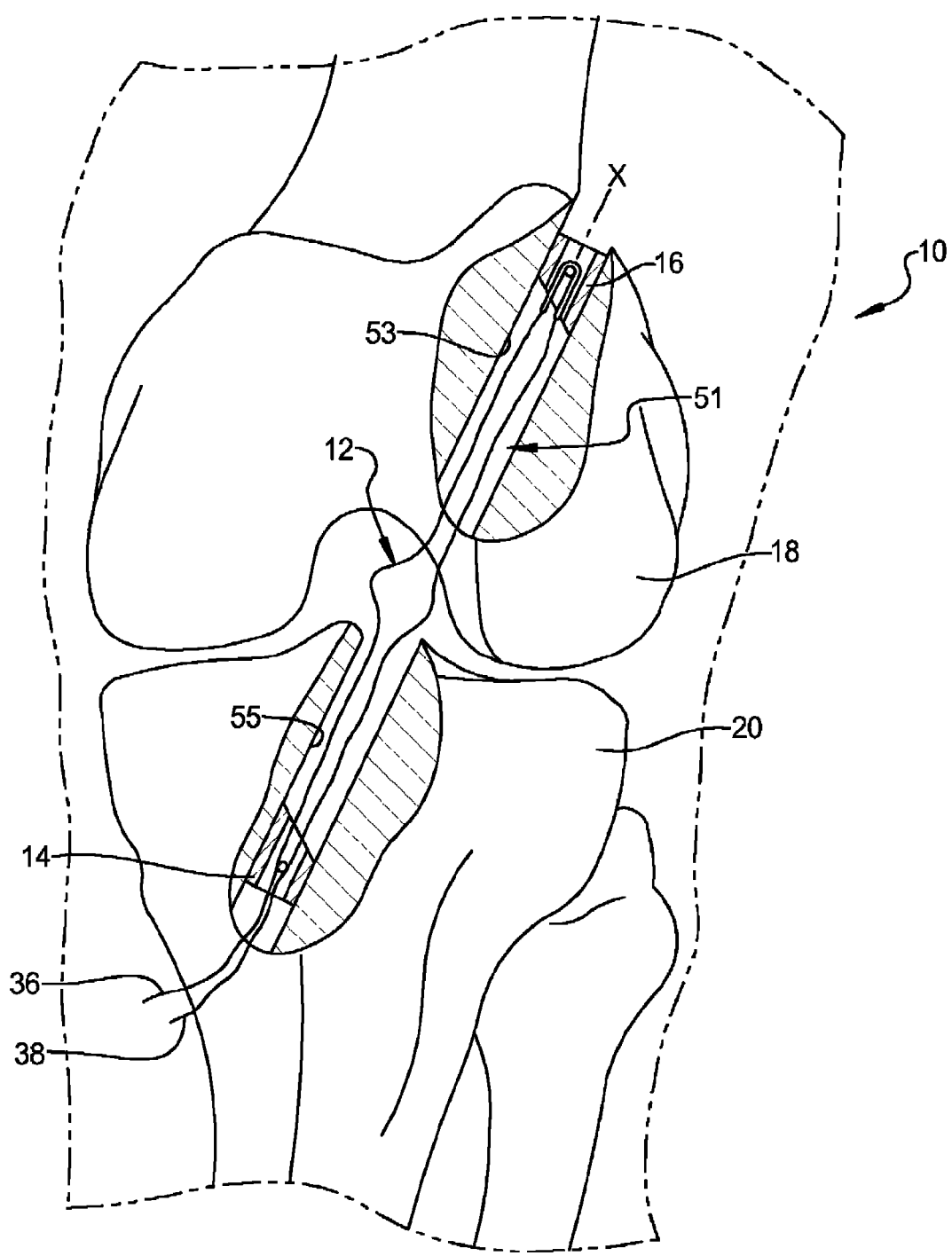
FIG. 7 is a section view of a knee joint during implantation of the system of FIG. 1, wherein the prosthetic ligament member thereof has low tension.

Moreover, an outer surface 50 of the base 40 of the fastener 14, 16 can be threaded along the longitudinal direction. Thus, as shown in FIGS. 7 and 8, the fasteners 14, 16 can be threadably and fixably attached to the tibia 20 and femur 18, respectively. It will be appreciated that the fasteners 14, 16 can be additionally attached to the tibia 20 and femur 18 by any additional means, such as bone cement, cross pins, additional fasteners, and the like.

As shown in FIGS. 3 and 4, the fasteners 14, 16 additionally include an attachment portion 52. In some embodiments, the attachment portion 52 can be a rod or post that extends transverse (e.g., perpendicular to the longitudinal axis of the fasteners 14, 16). The attachment portion 52 can be fixed at both ends to the interior walls of the base 40. Furthermore, as shown in FIG. 4, the attachment portion 52 can have a circular cross-section; however, the attachment portion 52 can have an ovate cross-section or any other suitable shape. Also, in some embodiments, the attachment portion 52 can be removably attached to the base 40 (e.g., inserted and removed in a direction transverse to the axis of the base 40).

Still further, the fasteners 14, 16 can be polygonal and/or can include at least one flat inner surface 54 (i.e., drive portion). For instance, in the embodiments represented in FIGS. 3 and 4, the fasteners 14, 16 can include a plurality of flat inner surfaces 54 adjacent the first end 42. As such, the flat inner surfaces 54 can collectively define an octagonal shape or any other suitable polygon.

It will be appreciated that the fasteners 14, 16 can have any suitable base 40 for attachment to the tibia 20 or femur 18 of the patient. Furthermore, it will be appreciated that the fasteners 14, 16 can have any suitable attachment portion 52 for operably coupling to the ligament member 12.

When attached to the first and second fasteners 14, 16 (FIG. 1), the ligament member 12 can be received in the hollow interior space 46 of each in order to operably connect to the respective attachment portions 52. More specifically, the first and second adjustable loops 32, 34 can extend continuously about (and encircle) the attachment portion 52 of the first fastener 14 in order to operably couple to the first fastener 14. Also, the longitudinal passage portion 26 can wrap, fold, or bend about the attachment portion 52 of the second fastener 16 to operably couple to the second fastener 16. Accordingly, by pulling on the first and second free ends 36, 38, the surgeon can tension the first and second loops 32, 34 and reduce the size of the first and second loops 32, 34 in order to tighten and tension the ligament member 12. This increase in tension can urge the first and second fasteners 14, 16 toward each other. Accordingly, when the first and second fasteners 14, 16 are attached to the tibia 20 and the femur 18, the increased tension can draw the tibia 20 and femur 18 together, and the tensioned ligament member 12 can constrain the tibia 20 and femur 18 relative to each other while permitting normal articulation of the knee joint. As such, the ligament member 12 can be used as an artificial prosthesis for replacing an anterior cruciate ligament, a posterior cruciate ligament, or any other suitable ligament.

It will be appreciated that the ligament member 12 can be coupled to the fasteners 14, 16 in any suitable fashion. For instance, in some embodiments, the first loop 32 can be attached to the first fastener 14, and the second loop 34 can be attached to the second fastener 16, or vice-versa. Moreover, the first and second ends 22, 24 can be routed through the first and second apertures 28, 30 in order to produce any suitable number of loops 32, 34, and those loops can be operably attached to the fasteners 14, 16 in any suitable fashion without departing from the scope of the present disclosure.

Moreover, it will be appreciated that the system 10 can be manufactured such that the ligament member 12 is preassembled and attached to the first and second fasteners 14, 16 before implantation surgery. Accordingly, the surgeon can attach the first and second fasteners 14, 16 to the tibia 20 and the femur 18, respectively, and the ligament member 12 will be substantially in position within the joint for tensioning. Thus, the system 10 can greatly facilitate repair and reconstruction of the knee joint. However, it will be appreciated that the system 10 can be such that the surgeon operably couples the ligament member 12 to the first fastener 14 and/or second fastener 16 intraoperatively without departing from the scope of the present disclosure.

Implantation of the system 10 will now be discussed in greater detail with reference to FIGS. 7 and 8. For purposes of discussion, the system 10 will be discussed in relation to replacement of an anatomical anterior cruciate ligament;

however, it will be appreciated that the system 10 can be used for any suitable ligament in the knee joint. It will be appreciated that the system 10 can be implanted during an arthroscopic surgical procedure.

Initially, the surgeon can make one or more incisions in the patient in order to at least partially expose the femur 18 and/or the tibia 20 of the patient. Then, the surgeon can form a bone tunnel 51, which includes a femur portion 53 and a tibia portion 55. The bone tunnel 51 can be formed using any suitable tool for removal of bone. More specifically, the surgeon can generally put the knee in flexion and drill through the tibia 20 into the femur 53 to form the tunnel 51. In some embodiments, the femur portion 53 of the tunnel 51 can be a blind bore.

Next, the surgeon can attach and fix the fastener 16 to the femur 18 and the fastener 14 to the tibia 20. In some embodiments, a tool 56, such as the type shown in FIG. 5, can be used to implant the first and second fasteners 14, 16. The tool 56 shown in FIG. 5 can include a head 58 with flat surfaces that correspond in shape to the flat interior surfaces 54 of the fasteners (FIGS. 3 and 4). Thus, the head 58 can mate with the flats of the interior surfaces 54, and the tool 56 can transmit rotational forces about the longitudinal axis of the fastener 14, 16 to drivingly rotate the fastener 14, 16. The tool 56 can also include a shaft 61 and a handle portion 63. Furthermore, in some embodiments, the tool 56 can include a clearance member 60, such as a groove 62 in the head 58 that provides clearance for the ligament member 12. More specifically, when the head 58 is mated with the fastener 14, 16, the ligament member 12 can extend along the groove 62 without impinging on the head 58. Thus, to implant the first and second fasteners 14, 16, the head 58 can be mateably inserted into the inner surface 54 of the respective fastener 14, 16, and the tool 56 can be rotated to threadably advance and attach the respective fastener 14, 16 to the tibia 20 or femur 18.

In other embodiments, the first and second fasteners 14, 16 can be implanted using the tool 56' shown in FIG. 6. The tool 56 includes a slot 64' and a clearance member 60' such as a cannula 66' that extends longitudinally through the tool 56'. Thus, during implantation, the tool 56' can mate with the respective fastener 14, 16, and the slot 64' can receive the attachment portion 52 of the respective fastener 14, 16 in order to rotatably engage the fastener 14, 16. Also, the ligament member 12 can be received within the cannula 66' during installation. It will be appreciated that the tool 56' can engage either end of the fasteners 14, 16 for greater versatility.

Assuming the ligament member 12 has already been coupled to both the first and second fasteners 14, 16, the free ends 36, 38 can extend out of the tibial portion 55 of the tunnel 51, away from the femur 18. In other embodiments, both free ends 36, 38 can extend out of the femoral portion 53 of the tunnel 51, away from the tibia 20. In still other embodiments, one of the free ends 36 can extend out of the tibial portion 55 of the tunnel 51, and the other free end 38 can extend out of the femoral portion 53 of the tunnel 51.

The surgeon can then pull on the first and second free ends 36, 38 to reduce the length of (i.e., eliminate slack in) the ligament member 12 and increase tension in the ligament member 12. Accordingly, the femur 18 and the tibia 20 can draw together and the ligament member 12 can be tensioned to support relative movement of the femur 18 and the tibia 20. Once the proper length and tension has been achieved, the surgeon can cut the first and second free ends 36, 38.

It will be appreciated that the fasteners 14, 16 of the system 10 can be made out of any suitable type, other than those shown in the embodiments of FIGS. 1-8. For instance, FIGS. 9-15 show additional features of the first and second fasteners that can be included within the system 10.

Figure 9:
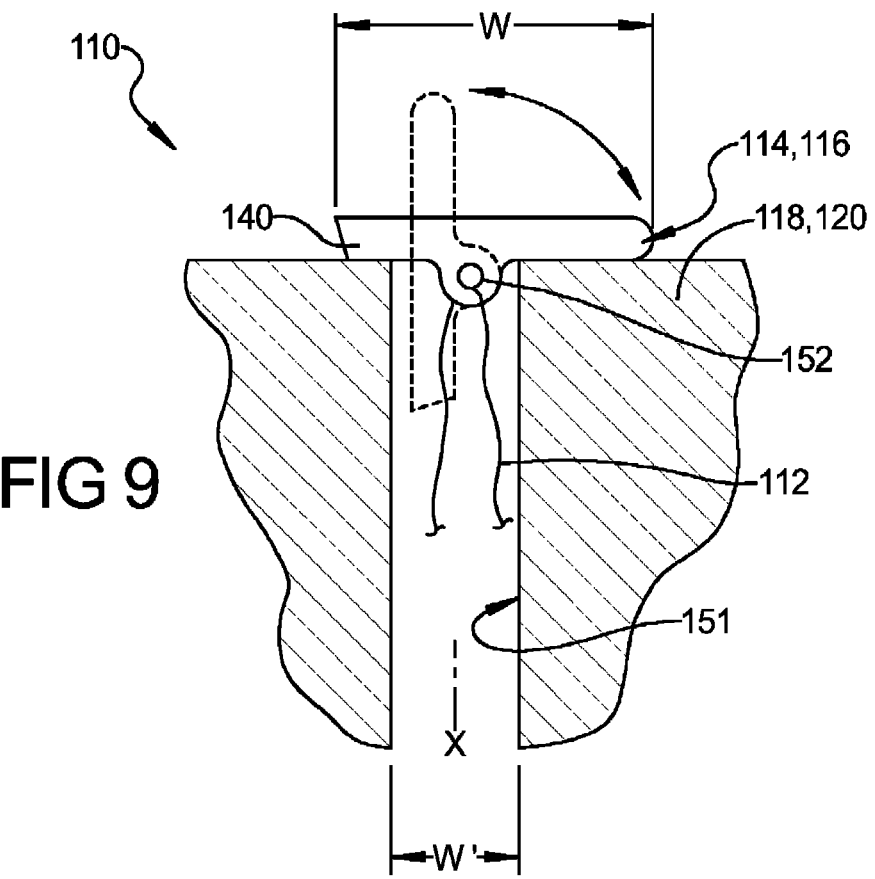
FIGS. 9-13 are side views of various fasteners of the system of FIG. 1 according to various additional embodiments.

For instance, FIG. 9 shows fastener 114, 116 of the system 110. Although only one fastener 114, 116 is shown in FIG. 9, it will be appreciated that each of the first and second fasteners 114, 116 can be similar to the illustrated embodiments. It will also be appreciated that components that are similar to the embodiments of FIGS. 1, 3, 4, 7, and 8 are identified with corresponding reference numerals increased by 100.

The fasteners 114, 116 can include an elongate base 140 and an attachment portion 152 that is attached to the base 140, similar to the TOGGLELOC™ fastener, which is commercially available from Biomet, Inc. of Warsaw, Ind. The base 140 and the attachment portion 152 can be made out of a substantially rigid material, such as a biocompatible metal, ceramic, polymer, or a composite thereof. More specifically, the fastener 114, 116 can be made out of titanium, cobalt chrome (CoCr), stainless steel, polyether ether ketone (PEEK), and/or RADEL polyphenylsulfone (PPSU). Furthermore, the fasteners 114, 116 can be of a type disclosed in Ser. No. 11/203,481 filed Aug. 12, 2005, now U.S. Patent Publication No. 2005-0277961, published Dec. 15, 2005, which is incorporated herein by reference in its entirety.

Also, the attachment portion 152 can be an eyelet that is integrally attached to the base 140 at a middle portion thereof. The ligament member 112 can be received in and threaded through (e.g., looped or partially wrapped around) the attachment portion 152, similar to the embodiments of FIGS. 1-8.

In addition, the fasteners 114, 116 can have a first position (shown in phantom lines) in which the base 140 is operable to move within the bone tunnel 151. The fasteners 114, 116 can also have a second position (shown in solid lines), in which the base 140 is operable to seat against the bone 118, 120 outside of the bone tunnel 151. More specifically, the base 140 can have a width W that is greater than the width W' of the bone tunnel 151. Thus, in the second position, the base 140 can be arranged so as to be transverse (e.g., perpendicular) to the axis X of the bone tunnel 151 in order to seat against the bone 118, 120. Also, in the first position, the base 140 can be arranged so as to be substantially aligned with the axis X of the bone tunnel 151 in order to move along the axis X of the bone tunnel 151.

Accordingly, during implantation of the system 110, the fastener 114, 116 can be moved along the axis X of the bone tunnel 151 in the first position, thereby pulling the ligament member 112 along the axis X. Then, once the fastener 114, 116 emerges from the tunnel 151, the fastener 114, 116 can be turned to the second position to seat against the bone 118, 120.

Figure 10:
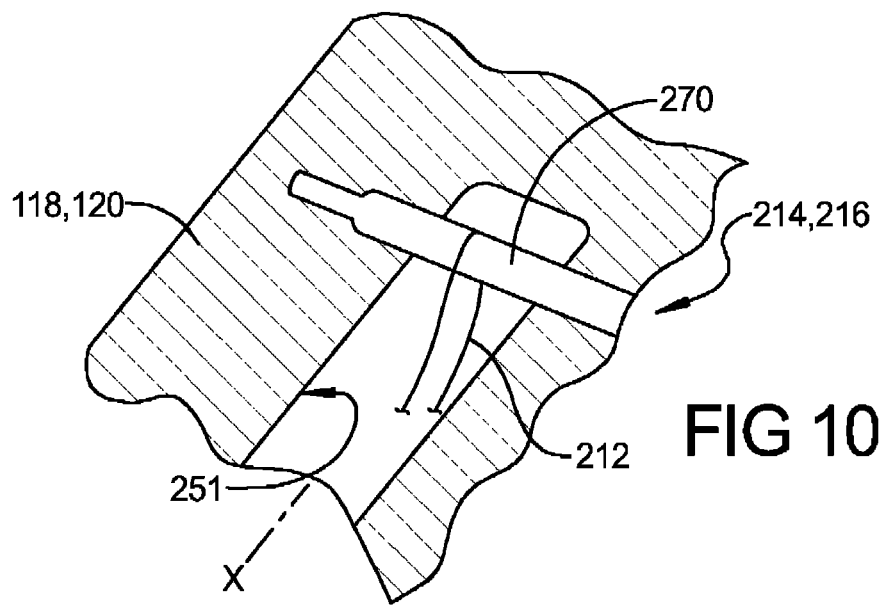

Referring now to FIG. 10, additional features of the fasteners 214, 216 are illustrated. Features that are common to those of the embodiments of FIGS. 1-8 are indicated with corresponding reference numerals increased by 200.

As shown in FIG. 10, the fasteners 214, 216 can include an elongate cross pin 270. The pin 270 can be embedded within and attached to the femur 218 or tibia 220. More specifically, the pin 270 can extend transversely to the axis X of the bone tunnel 251, and can extend across the bone tunnel 251 to be secured at both ends in the femur 218 or tibia 220. Furthermore, the ligament member 212 can extend about the pin 270 in order to operably attach to the pin 270. It will be appreciated that the fastener 214, 216 can include various features to those disclosed in Ser. No. 11/059,869 filed Feb. 16, 2005, now U.S. Patent Publication No. 2005-0149187, published Jul. 7, 2005, which is hereby incorporated by reference in its entirety.

Figure 11:
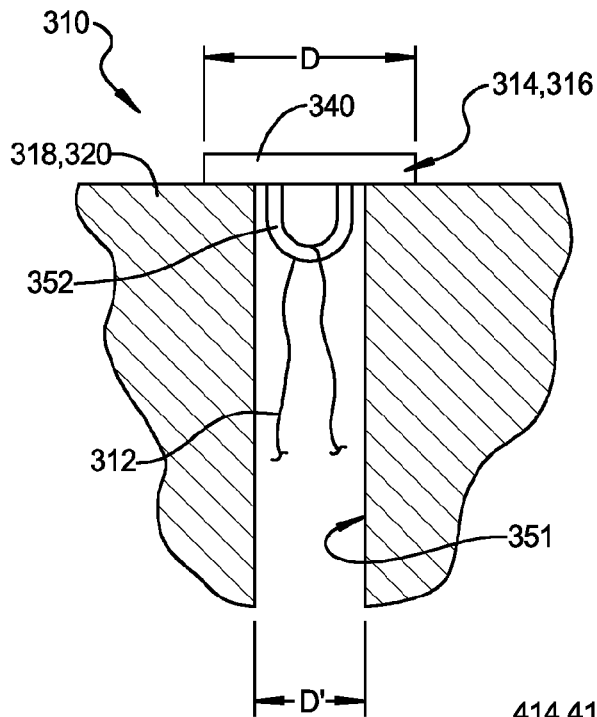

Referring now to FIG. 11, additional features of the fasteners 314, 316 are illustrated. Features that are similar to the embodiments of FIGS. 1-8 are indicated with corresponding reference numerals increased by 300.

The fasteners 314, 316 can include a base 340 that is disk-shaped and attachment portion 352 (e.g., an eyelet) that is integrally attached to the base 340, so as to be monolithic. The diameter D of the base 340 can be greater than the diameter D' of the bone tunnel 351. Accordingly, the base 340 can seat to the bone 318, 320 to thereby secure the base 340 to the bone 318, 320. Moreover, the ligament member 312 can be received within and can extend through the attachment portion 352. More specifically, the attachment portion 352 can extend continuously about the ligament member 312 to thereby encircle the ligament member 312. As such, the attachment portion 352 can inhibit movement of the ligament member 312 outside of the attachment portion 352. As stated above, the ligament member 312 can be manufactured and supplied to the surgeon pre-attached to the attachment portion 352. Alternatively, the system 310 can be employed such that the surgeon threads the attachment portion 312 through the attachment portion 352 intraoperatively.

Figure 12:
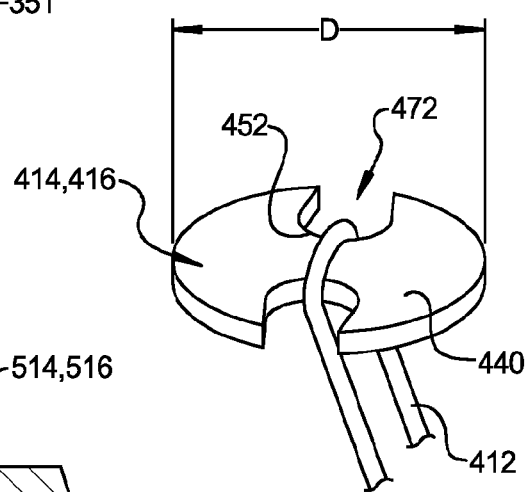

Referring now to FIG. 12, additional features of the fasteners 414, 416 are illustrated. Components that are similar to the embodiments of FIGS. 1-8 are indicated with corresponding reference numerals increased by 400.

The fasteners 414, 416 can include a base 440 and an attachment portion 452. The base can be substantially disk-shaped and can have a diameter D that is greater than the diameter of the bone tunnel (not shown), such that the base 440 can seat against the bone, similar to the embodiments of FIG. 11. The attachment portion 452 can include one or more openings 472 (e.g., notches, slots, etc.) that extend inwardly from the outer periphery of the base 440. The ligament member 412 can extend over the base 440 and can be received in the openings 472 to be retained therein. For instance, the ligament member 412 can be looped or at least partially wrapped around the base 440 to be received in the openings 472. It will be appreciated that the openings 472 allow the ligament member 412 to selectively move in and out of the attachment portion 452. Accordingly, the surgeon can intraoperatively attach and detach the ligament member 412 from the fastener 414, 416.

Figure 13:
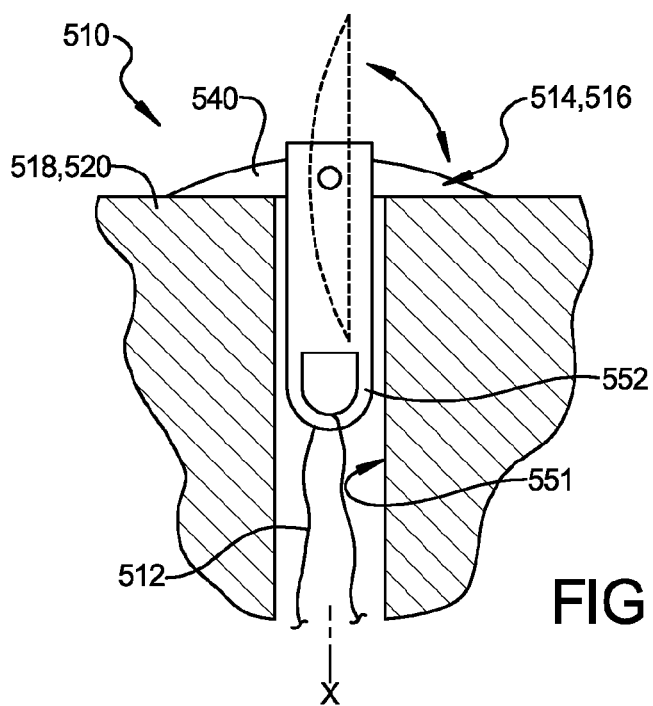

Referring now to FIG. 13, additional features of the fasteners 514, 516 are illustrated. Components that are similar to the embodiments of FIGS. 1-8 are indicated by corresponding reference numerals increased by 500.

The fasteners 514, 516 can be similar to EZLOC™ fasteners, which are commercially available from Biomet, Inc. of Warsaw, Ind. Furthermore, the fasteners 514, 516 can include various features of the type disclosed in Ser. No. 12/047,048 filed Mar. 12, 2008, now U.S. Patent Publication No. 2008-0161852, published Jul. 3, 2008, which is hereby incorporated by reference in its entirety. Accordingly, the fasteners 514, 516 can include a base 540 and an attachment portion 552. The attachment portion 552 can receive the ligament member 512. For instance, the ligament member 512 can loop around or at least partially wrap around the ligament member 512 to attach to the fastener 514, 516.

Moreover, the base 540 can be movably (e.g., pivotally) attached to the attachment portion 552. As such, the fastener 514, 516 can be selectively collapsible and extendable. More specifically, in the collapsed position (partially shown in phantom), the base 540 can be rotated relative to the attachment portion 552 such that the fastener 514, 516 is substantially aligned with the axis X of the bone tunnel 551, thereby allowing the fastener 514, 516 to move along the axis X of the bone tunnel 551. In addition, when the fastener 514, 516 is extended, the base 540 can be rotated to be substantially perpendicular to the axis X of the bone tunnel 551, and the base 540 can seat against the femur 518 or tibia 520. Accordingly, during implantation of the system 510, the fastener 514, 516 can be collapsed and moved through the tunnel 551, thereby pulling the ligament member 512 along the axis X of the tunnel 551. Then, when the base 540 sufficiently emerges from the tunnel 551, the fastener 514, 516 can be selectively moved to the extended position, such that the base 540 can be seated.

Figure 14:
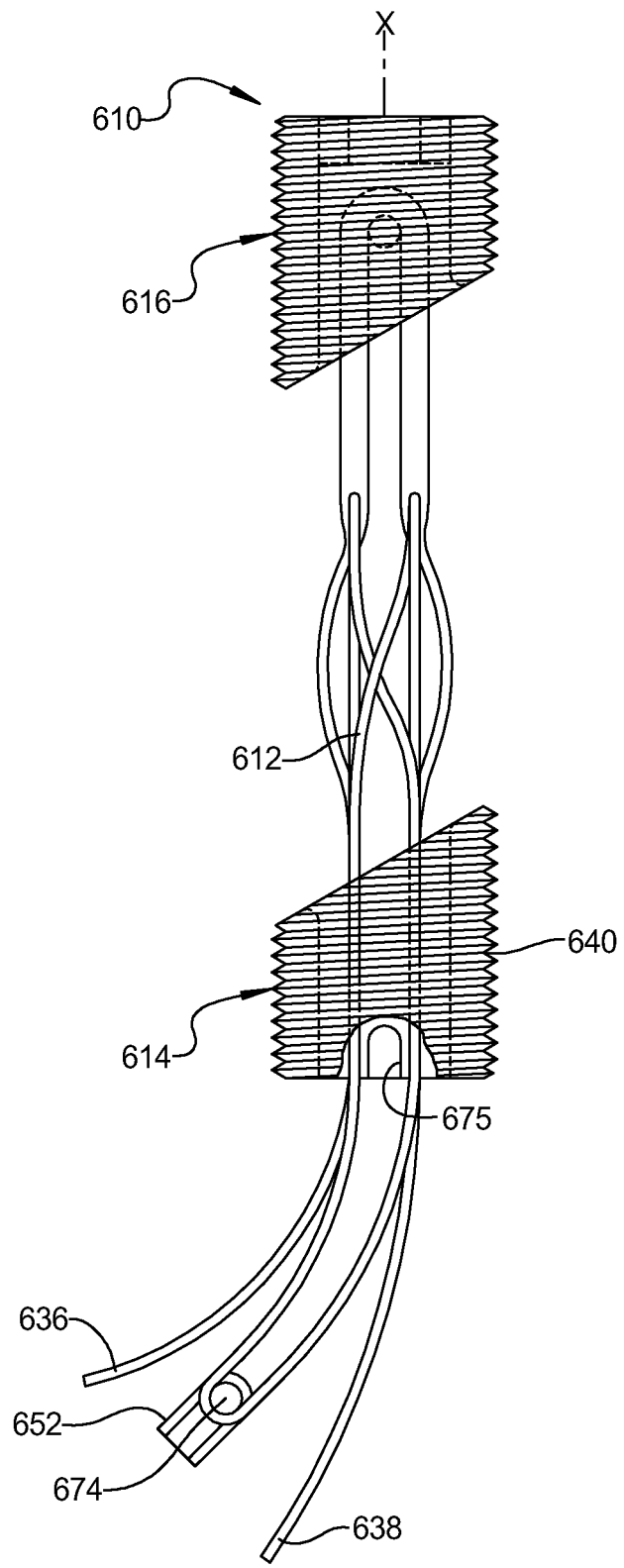
FIG. 14 is a side view of the system of FIG. 1 according to various other embodiments.

Referring now to FIG. 14, additional features of the fasteners 614, 616 are illustrated. Components that are similar to the embodiments of FIGS. 1-8 are indicated with corresponding reference numerals increased by 600.

As shown, the fasteners 614, 616 can be substantially similar to the embodiments of FIGS. 1, 3, 4, 7, and 8. However, the fasteners 614 can include a base 640 and a removably attached attachment portion 652. It will be appreciated that the fasteners 616 can also include a removably attached attachment portion 652. The attachment portion 652 can include one or more projections 674, such as posts, rails, and the like. The projections 674 can be received within a corresponding recess 675, such as a slot, within the base 640 in order to lock (i.e., key) the attachment portion 652 against rotation about the axis X relative to the base 640. It will be appreciated that the base 640 could include projections 674 and the attachment portions 652 could include corresponding recesses that receive the projection 674, without departing from the scope of the present disclosure. It will also be appreciated that the attachment portion 652 could be keyed against rotation about the axis X in any suitable manner.

Implantation of the system 610 will be discussed, with the assumption that the ligament member 612 is attached to the second fastener 616 and also to the attachment portion 652 of the first fastener 614. The first fastener 616 can be threadably attached to the femur (not shown). Similarly, the second fastener 616 can be threadably attached to the tibia (not shown). It will be appreciated that the ligament member 612 could become twisted helically about the axis X during the attachment of the second fastener 616 and/or the attachment of the base 640 of the first fastener 614. However, because the attachment portion 652 remains detached from the base 640, the surgeon can untwist the ligament member 612 and subsequently pull on the free ends 636, 638 in order to draw the attachment portion 652 into the base 640 and key the attachment portion 652 against rotation about the axis X. As such, the ligament member 612 can be substantially untwisted and yet the ligament member 612 can be securely attached to both the first and second fasteners 614, 616.

Figure 15:
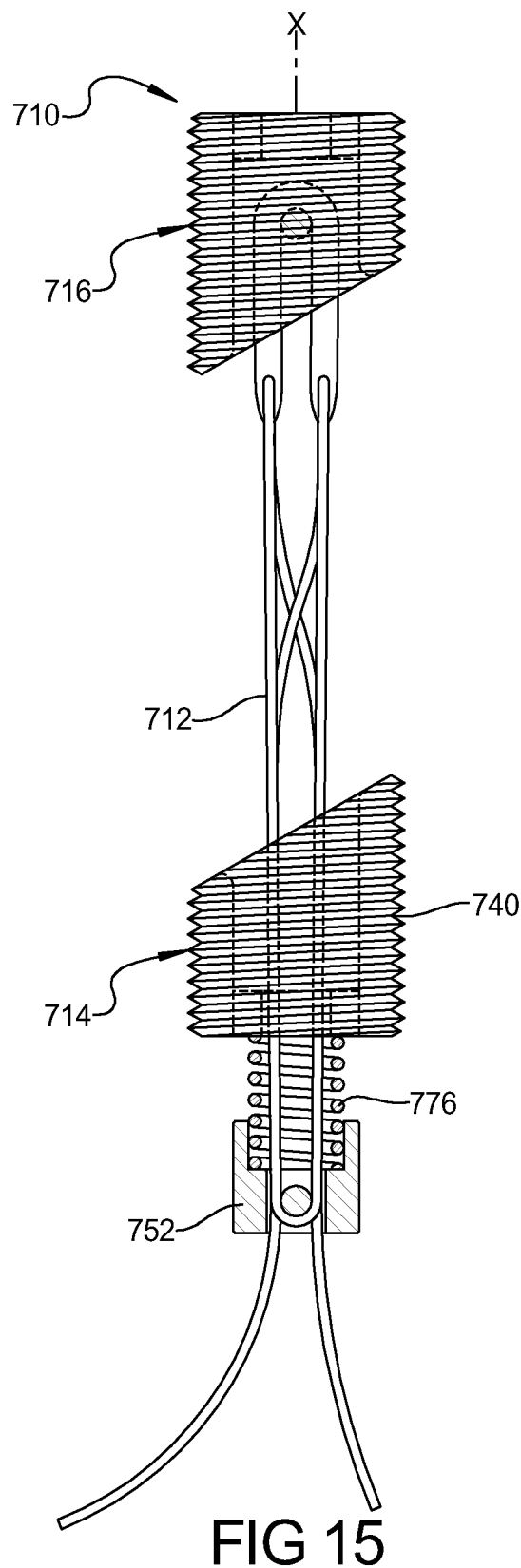
FIG. 15 is a side view of the system of FIG. 1 according to various other embodiments.

Referring now to FIG. 15, additional features of the fastener 714, 716 will be described in greater detail. Components that are similar to the embodiments of FIGS. 1-8 are indicated by corresponding reference numerals increased by 700.

The second fastener 716 can be substantially similar to the second fasteners of the embodiments described above. However, the first fastener 714 can include different features which will be described herein below. It will be appreciated that the second fastener 716 can include the same features as the first fastener 714 without departing from the scope of the present disclosure.

The first fastener 714 can include a base 740 and an attachment portion 752. The attachment portion 752 can be detached and spaced away from the base 740. Moreover, the system 710 can include a biasing member 776. The biasing member 776 can be made out of any suitable type, such as a helical spring, one or more Belleville washers (coned-disk spring washer), etc. The biasing member 776 can be disposed between and can abut the base 740 and the attachment portion 752. Accordingly, the biasing member 776 can bias the attachment portion 752 away from the base 740 to thereby maintain a predetermined amount of tension in the ligament member 712.

It will be appreciated that the prosthetic ligament system of the present disclosure can be attached to the patient's anatomy using any combination of the fasteners 14, 16, 114, 116, 214, 216, 314, 316, 414, 416, 514, 516, 614, 616, 714, 716 disclosed herein. Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A system for a knee joint with a tibia and a femur, the system comprising:
    a first fastener operable to be connected to the tibia;
    a second fastener operable to be connected to the femur; and
    a prosthetic ligament member that is flexible, the ligament member directly coupled to both the first and second fasteners to support the tibia and the femur for relative movement, the ligament member extending from a first end to a second end, the ligament member including an outer wall that defines a hollow longitudinal passage portion having a first end and a second end, the first end of the ligament member extending into the first end of the longitudinal passage portion through the outer wall and out of the second end of the longitudinal passage portion through the outer wall to define a first adjustable loop, the second end extending into the second end of the longitudinal passage portion through the outer wall and out of the first end of the longitudinal passage portion through the outer wall to define a second adjustable loop, wherein the ligament member is an integrated one-piece device.

2. The system of claim 1, wherein both the first and second adjustable loops are selectively adjustable to adjust a tension in the ligament member.

3. The system of claim 1, wherein the first end of the ligament member also includes a first free end, wherein the second end of the ligament member also includes a second free end, the first free end pullable to reduce a size of the first adjustable loop, the second free end pullable to reduce a size of the second adjustable loop.

4. The system of claim 3, wherein the first and second free ends are cuttable.

5. The system of claim 1, wherein the ligament member includes a plurality of apertures extending through the outer wall, wherein the first end of the ligament member enters the longitudinal passage portion through a different aperture from which the second end of the ligament member exits the longitudinal passage portion, and wherein the second end of the ligament member enters the longitudinal passage portion through a different aperture from which the first end of the ligament member exits the longitudinal passage portion.

6. The system of claim 1, wherein the ligament member includes a plurality of braided fibers.

7. The system of claim 1, wherein the first and second adjustable loops are limited from enlargement due to friction between an interior surface of the longitudinal passage portion, the first end of the ligament member, and the second end of the ligament member.

8. The system of claim 1, wherein at least one of the first and second fasteners includes a base and an attachment portion, and wherein the ligament member is operable to be received in a tunnel formed in one of the tibia and the femur, the ligament member extending about the attachment portion to operably couple to the attachment portion.

9. The system of claim 8, wherein the attachment portion extends continuously about the ligament member to thereby encircle the ligament member and inhibit movement of the ligament member outside the attachment portion.

10. The system of claim 8, wherein the attachment portion includes an opening allowing the ligament member to selectively move in and out of the attachment portion.

11. The system of claim 1, wherein at least one of the first and second fasteners is chosen from a group consisting of:
    a pin operable to be embedded within and attached to one of the femur and the tibia to extend transversely across a tunnel formed within the one of the femur and the tibia, wherein the ligament member is operable to be received in the tunnel and extend about the pin to operably couple to the pin; and
    a first base and a first attachment portion, wherein the first base has a first position in which the first base is operable to move within a tunnel formed in one of the femur and the tibia, wherein the first base has a second position in which the first base is operable to seat against the one of the femur and the tibia outside the tunnel, and wherein the ligament member is operable to be received in the tunnel and extend about the first attachment portion to operably couple to the first attachment portion, wherein the first base is rigid, wherein, in the first position, an axis of the first base is substantially aligned with a longitudinal axis of the tunnel, and wherein, in the second position, the axis of the first base is transverse to the longitudinal axis of the tunnel.

12. The system of claim 1, wherein at least one of the first and second fasteners includes a base, and further comprising an attachment portion that is separate from the base, the base being operable to be connected to the corresponding one of the tibia and the femur, the ligament member being coupled to the attachment portion, and further comprising a biasing member that is disposed between and abuts the base and the attachment portion and that is operable to bias the attachment portion and the base away from each other to tension the ligament member.

13. The system of claim 1, wherein at least one of the first and second fasteners includes a base and an attachment portion, wherein the base has a first position in which the base is operable to move within a tunnel formed in one of the femur and the tibia, wherein the base has a second position in which the base is operable to seat against the one of the femur and the tibia outside the tunnel, and wherein the ligament member is operable to be received in the tunnel and extend about the attachment portion to operably couple to the attachment portion, wherein the base is moveably attached to the attachment portion such that the one of the first and second fastener is selectively collapsible and expandable, wherein, in the first position, the one of the first and second fastener is collapsed to allow the base and the attachment portion to move within the tunnel, and wherein, in the second position, the one of the first and second fastener is extended to seat outside the tunnel.

14. A system for a knee joint with a tibia and a femur, the system comprising:
a first fastener operable to be connected to the tibia;
a second fastener operable to be connected to the femur; and
a prosthetic ligament member that is flexible and that is operably coupled to both the first and second fasteners to support the tibia and the femur for relative movement, the ligament member extending from a first end to a second end, the ligament member including an outer wall that defines a hollow longitudinal passage portion, the ligament member also including at least one first aperture extending through the outer wall and disposed between the first and second ends, the ligament member further including at least one second aperture extending through the outer wall and disposed between the first and second ends, the at least one first and second apertures being disposed at opposite ends of the longitudinal passage portion, the first end of the ligament member extending through the at least one first aperture and the longitudinal passage portion and out of the at least one second aperture to define a first adjustable loop and a first free end, the second end of the ligament member extending through the at least one second aperture and the longitudinal passage portion and out of the at least one first aperture to define a second adjustable loop and a second free end, the first and second free ends pullable to increase a tension in the ligament member, wherein the first adjustable loop is directly coupled to one of the first and second fasteners and the second adjustable loop is directly coupled to the other one of the first and second fasteners.

15. The system of claim 14, wherein both the first and second adjustable loops encircle a portion of the first fastener and the outer wall is folded over a portion of the second fastener such that both the first and second adjustable loops are directly coupled to both the first and second fasteners.

16. A system for a knee joint with a tibia and a femur, the system comprising:
a first fastener;
a second fastener; and
a prosthetic ligament member that is flexible and that is operably coupled to at least one of the first fastener and the second fastener, the prosthetic ligament member extending from a first end to a second end, the ligament member including an outer wall that defines a hollow longitudinal passage, the ligament member also including a first aperture, a second aperture, a third aperture, and a fourth aperture extending through the outer wall into the hollow longitudinal passage and disposed between the first and second ends, the first end extending into the first aperture and out the second aperture and through at least a portion of the longitudinal passage to define a first adjustable loop and a first free end, the first and second apertures being disposed at opposite ends of the portion of the longitudinal passage through which the first end extends, the second end extending into the third aperture and out the fourth aperture and through at least a portion of the longitudinal passage to define a second adjustable loop and a second free end, the third and fourth apertures being disposed at opposite ends of the portion of the longitudinal passage through which the second end extends, the first and second adjustable loops extending from the first fastener and the first and second free ends pullable to increase a tension in the ligament member.

17. The system of claim 16, wherein the first and second adjustable loops extend from the first fastener and are adjustably coupled to the second fastener.

* * * * *